United States Patent
Jain et al.

(10) Patent No.: US 9,174,943 B2
(45) Date of Patent: Nov. 3, 2015

(54) PROCESSES FOR THE SYNTHESIS OF DIARYLTHIOHYDANTOIN AND DIARYLHYDANTOIN COMPOUNDS

(71) Applicants: Rajendra Parasmal Jain, Pune (IN); Remy Angelaud, Union, NJ (US); Andrew Thompson, Mountainside, NJ (US); Carol Lamberson, Ringoes, NJ (US); Scott Greenfield, Delmar, NY (US)

(72) Inventors: Rajendra Parasmal Jain, Pune (IN); Remy Angelaud, Union, NJ (US); Andrew Thompson, Mountainside, NJ (US); Carol Lamberson, Ringoes, NJ (US); Scott Greenfield, Delmar, NY (US)

(73) Assignee: MEDIVATION PROSTATE THERAPEUTICS, INC., San Francisco, CA (US)

( * ) Notice: Subject to any disclaimer, the term of this patent is extended or adjusted under 35 U.S.C. 154(b) by 0 days.

(21) Appl. No.: 13/785,504

(22) Filed: Mar. 5, 2013

(65) Prior Publication Data
US 2013/0190507 A1 Jul. 25, 2013

Related U.S. Application Data

(63) Continuation of application No. 13/580,718, filed as application No. PCT/US2011/026135 on Feb. 24, 2011, now abandoned.

(60) Provisional application No. 61/307,796, filed on Feb. 24, 2010.

(51) Int. Cl.
| C07D 233/86 | (2006.01) |
| C07D 235/02 | (2006.01) |
| C07D 233/40 | (2006.01) |
| C07D 233/42 | (2006.01) |

(52) U.S. Cl.
CPC ............ *C07D 233/86* (2013.01); *C07D 235/02* (2013.01)

(58) Field of Classification Search
USPC .......... 548/301.1, 301.4, 321.1, 320.1, 320.5, 548/300.7
See application file for complete search history.

(56) References Cited

U.S. PATENT DOCUMENTS

| 2,884,448 A | 4/1959 | Mosby et al. |
| 3,684,774 A | 8/1972 | Merten et al. |
| 4,424,396 A | 1/1984 | Simon-Bierenbaum et al. |
| 5,235,093 A | 8/1993 | Cova et al. |
| 2004/0116417 A1 | 6/2004 | Boubia et al. |
| 2007/0254933 A1* | 11/2007 | Jung et al. ............... 514/387 |
| 2009/0170920 A1 | 7/2009 | Chen et al. |
| 2010/0190991 A1 | 7/2010 | Ouerfelli et al. |
| 2010/0210665 A1 | 8/2010 | Sawyers et al. |

FOREIGN PATENT DOCUMENTS

| EP | 1790640 A1 | 5/2007 |
| WO | 2006124118 A1 | 11/2006 |
| WO | 2007/126765 A2 | 11/2007 |
| WO | 2008/093838 A1 | 8/2008 |
| WO | 2008119015 A2 | 10/2008 |
| WO | 2010099238 A1 | 9/2010 |
| WO | 2010118354 A1 | 10/2010 |

OTHER PUBLICATIONS

Extended European Search Report for EP Application Serial No. 11748095.4, dated Sep. 26, 2013.
International Search Report for PCT/US11/26135 mailed Apr. 27, 2011.
Third Party Observations filed in EP Application No. 11748095.4, filed Feb. 9, 2015.
Jain & Chakravarty, "Substituted D-arylhydantoin and Di-arylthiohydantoin Compounds and Methods for Use Thereof," Indian patent application 731/DEL/2009 filed Apr. 9, 2009.
Chakravarty & Jain, "Substituted D-arylhydantoin and Di-arylthiohydantoin Compounds and Methods for Use Thereof," U.S. Appl. No. 61/173,438, filed Apr. 28, 2009.
Chakravarty & Jain, "Substituted Phenylcarbamoyl Alkylamino Arene Compounds and N,N'-bis-Arylurea Compounds," U.S. Appl. No. 61/249,532, filed Oct. 7, 2009.

* cited by examiner

*Primary Examiner* — Joseph Kosack
*Assistant Examiner* — Amanda L Aguirre
(74) *Attorney, Agent, or Firm* — Banner & Witcoff, Ltd.

(57) ABSTRACT

Processes are provided for the synthesis of diarylthiohydantoin and diarylhydantoin compounds. Medicinal products containing the same find particular use in treating prostate cancer, including castration-resistant prostate cancer and/or hormone-sensitive prostate cancer.

20 Claims, No Drawings

PROCESSES FOR THE SYNTHESIS OF DIARYLTHIOHYDANTOIN AND DIARYLHYDANTOIN COMPOUNDS

CROSS-REFERENCE TO RELATED APPLICATIONS

This patent application is a continuation of Ser. No. 13/580,718 filed Aug. 23, 2012 as a national phase application of PCT/US2011/026135 filed on Feb. 24, 2011, which claims priority to Ser. No. 61/307,796, filed Feb. 24, 2010. Each of these applications is incorporated herein by reference in its entirety.

STATEMENT REGARDING FEDERALLY SPONSORED RESEARCH OR DEVELOPMENT

Not applicable.

FIELD OF THE INVENTION

The invention is in the field of cancer therapeutics, such as processes for the synthesis of prostate cancer therapeutics.

BACKGROUND OF THE INVENTION

According to the American Cancer Society, prostate cancer is the most commonly diagnosed cancer among men in the United States, other than skin cancer. The American Cancer Society estimates that approximately 186,000 new cases of prostate cancer were diagnosed, and approximately 29,000 men died of prostate cancer in the United States alone during 2008. Prostate cancer is thus the second-leading cause of cancer death in men in the United States, after lung cancer.

Metastatic prostate cancer is cancer that has spread beyond the prostate and surrounding tissues into distant organs and tissues. The majority of men who die from prostate cancer die from the consequences of metastatic disease. According to the National Cancer Institute, the median survival of patients with prostate cancer that has metastasized to distant organs is usually one to three years, and most such patients will die of prostate cancer. Metastatic prostate cancer is generally divided into two states: the hormone-sensitive state and the castration-resistant state (also referred to as the hormone-refractory state).

Testosterone and other male sex hormones, known collectively as androgens, can fuel the growth of prostate cancer cells. Androgens exert their effects on prostate cancer cells by binding to and activating the androgen receptor, which is expressed in prostate cancer cells. When they first metastasize to distant sites, most prostate cancers depend on androgens for growth. These prostate cancers are known as "hormone-sensitive" cancers. Accordingly, the leading therapies currently used for the treatment of metastatic prostate cancer are focused on diminishing, or antagonizing, the effects of androgens on prostate cancer cells. One approach utilizes so-called "anti-androgens," which are molecules that block the interaction of androgens with the androgen receptor. Another approach is to reduce the amount of androgens produced in the body, primarily in the testes. This can be achieved surgically by removal of both testicles (orchiectomy) or through use of drugs known as luteinizing hormone-releasing hormone, or LHRH, agonist drugs, which lower the native production of testosterone in the testicles (sometimes called "chemical castration").

Most metastatic prostate cancer initially is hormone-sensitive and thus responds to hormonal therapies. However, according to a study published in the Oct. 7, 2004 issue of *The New England Journal of Medicine*, virtually all hormone-sensitive metastatic prostate cancer undergoes changes that convert it to the castration-resistant state in a median of 18-24 months after initiation of hormonal therapy [Debes, J. et al. "Mechanisms of Androgen-Refractory Prostate Cancer." New. England. J. Med. (2004), 351:1488-1490]. One of the important mechanisms by which prostate cancer cells switch from the hormone-sensitive to the castration-resistant state appears to be through overexpression of the androgen receptor. In experiments comparing gene expression in hormone sensitive and castration-resistant prostate cancer cells, an increase in androgen receptor expression was the only gene change consistently associated with castration-resistant disease [Chen, C. et al. "Molecular determinants of resistance to antiandrogen therapy." Nat. Med. (2004), 10(1):33-39]. Once in this state, prostate cancers generally continue to grow in an androgen-dependent manner despite the reduction of testosterone production to very low (i.e., post-castration) levels. Prostate cancer in this state is known as "castration-resistant" prostate cancer, or CRPC. The switch from the hormone-sensitive to the castration-resistant state following initiation of hormonal therapy is generally determined based on either rising levels of prostate-specific antigen, or PSA, or documented disease progression as evidenced by imaging tests or clinical symptoms. Metastatic prostate cancer that has become castration-resistant is extremely aggressive; these patients have a median survival of only 10 to 16 months.

A primary reason that CRPC is so deadly is that it is difficult to treat. Because therapies currently used for the treatment of metastatic prostate cancer operate by reducing the ability of androgens to fuel the growth of prostate cancer cells, they generally are effective only on prostate cancers that remain hormone-sensitive by depending on androgens for growth. CRPC no longer responds to hormonal therapies that are effective in the hormone-sensitive state. To further complicate the situation, due to biological changes in prostate cancer that has entered the castration resistant state, drugs that initially block the androgen receptor and inhibit growth of hormone sensitive prostate cancer may have precisely the opposite effect and start to fuel the growth of CRPC. For example, Casodex® (bicalutamide), sold by AstraZeneca PLC, directly blocks the interaction of androgens with the androgen receptor and is the largest selling of the anti-androgen therapies. However, in an in vitro model of castration-resistant prostate cancer in which prostate cancer cell lines were genetically engineered to overexpress the androgen receptor (thus converting them from the hormone-sensitive to the castration-resistant state), Casodex® failed effectively to inhibit the androgen receptor in these cells, and in some cases it became a stimulant of the androgen receptor. These findings, which are consistent with the published human clinical experience with Casodex in CRPC, render Casodex® an ineffective therapy for the castration-resistant state of metastatic prostate cancer.

Compounds that bind the androgen receptor, the same target bound by Casodex® and other marketed drugs for metastatic prostate cancer, have been developed for use in the castration-resistant state of metastatic prostate cancer. These compounds bind the androgen receptor in a manner that renders them effective in treating cancers that have become refractory to currently used drugs. For example, certain compounds disclosed in U.S. Patent Application Publication Nos. 2007/0004753, 2007/0254933 (republished as 2008/0139634), and 2009/0111864 are novel small-molecule androgen receptor antagonists that inhibit androgen receptor function by blocking nuclear translocation of the androgen receptor and DNA binding.

The synthetic route to compounds of the invention, as described in the aforementioned U.S. patent application Publications, comprises the coupling of an isothiocyanate with an isobutyronitrile. The main drawbacks of the process as previously described include only a 25% yield of desired product being achieved in the final step, resulting in a 15% overall yield from commercially available starting materials. Moreover, each intermediate compound requires laborious column chromatography for purification, resulting in extended overall production time which is industrially disadvantageous. In comparison, the present invention described herein comprises a 50% overall yield, and any required purification is achieved by simple precipitation or crystallization means. Further, the present invention avoids the use of the extremely toxic reagent acetone cyanohydrin. As a result, the process according to the present invention is a safer process in which the amount of solvent is lowered, minimizing waste and environmental impact, the cycle time is reduced, and the throughput and overall yield of the process is increased.

BRIEF SUMMARY OF THE INVENTION

The present invention comprises a highly efficient process for making a compound of formula (I, 2-I):

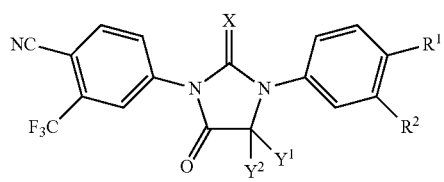

wherein:
X is S or O;
$Y^1$ and $Y^2$ are independently methyl or, together with the carbon to which they are attached, form a cycloalkyl group of 4 to 5 carbon atoms;
$R^1$ is $L^1$-C(=O)—$NR^4R^5$, or $L^1$-CN; where $L^1$ is a single bond or $C_1$-$C_8$ alkylene; and
$R^4$ and $R^5$ are independently selected from H and $C_1$-$C_8$ alkyl; and
$R^2$ is hydrogen or fluoro;
said process comprising reacting the compound of formula A:

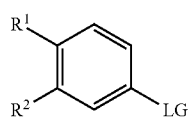

wherein LG is Br, I or another good leaving group, with a compound of formula B:

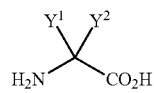

to yield a compound of formula C:

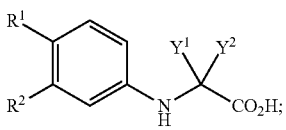

reacting the compound of formula C with a compound of formula $R^6$-LG under alkylating conditions or with a compound of formula $R^6$—OH under esterification conditions to form the compound of formula D:

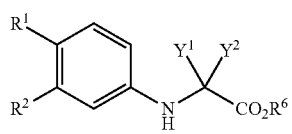

wherein $R^6$ is $C_1$-$C_8$ alkyl;
and reacting the compound of formula D with the compound of formula (F,2-F):

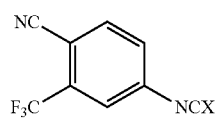

where X is S or O,
to yield the diarylthiohydantoin or diarylhydantoin compound of formula (I, 2-1):

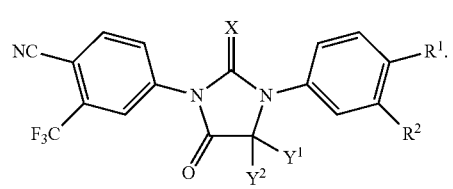

In one embodiment, with respect to the compounds of formula A, LG is Br or I. In a particular embodiment, LG is Br.

Another aspect of the present invention provides an efficient method of making an acid compound of formula (I, 2-Ia):

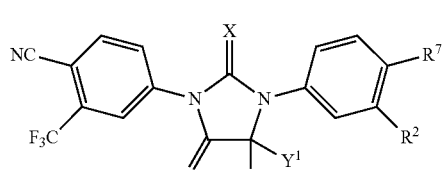

wherein:
Y¹ and Y² are independently methyl or, together with the carbon to which they are attached, form a cycloalkyl group of 4 to 5 carbon atoms;
R⁷ is L¹-C(=O)—OH; where L¹ is a single bond or $C_1$-$C_8$ alkylene; and
R² is hydrogen or fluoro;
said process comprising hydrolysis of a compound of formula I, 2-I:

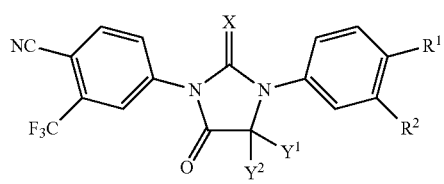

I, 2-I wherein
R¹ is L¹-C(=O)—NR⁴R⁵; where L¹ is a single bond or $C_1$-$C_8$ alkylene; and R⁴ and R⁵ are independently selected from H and $C_1$-$C_8$ alkyl.

In one particular embodiment, with respect to the compound of formula I, 2-Ia, L¹ is a single bond; and R⁷ is —C(=O)—OH.

In one particular embodiment, with respect to the compound of formula I, 2-Ia, Y¹ and Y² are both methyl, R⁷ is —C(=O)—OH, and R² is F.

In one embodiment, the above hydrolysis is carried out in the presence of concentrated HCl.

In one embodiment, the above hydrolysis is carried out at 80-140° C. or at about 80-140° C.

In one particular embodiment, the above hydrolysis is carried out at 120° C. or at about 120° C.

In one embodiment, the above hydrolysis is carried out for 10-60 hr or for about 10 hr to about 60 hr.

In one particular embodiment, the above hydrolysis is carried out for 48 hr or for about 48 hr.

In one particular embodiment, with respect to the compound of formula I, 2-Ia, X is S.

In one particular embodiment, with respect to the compound of formula I, 2-Ia, X is O.

In one particular embodiment, with respect to the compound of formula I, 2-Ia, Y¹ and Y² are both methyl, R⁷ is —C(=O)—OH, R² is F, and X is S.

In one particular embodiment, with respect to the compound of formula I, 2-Ia, Y¹ and Y² are both methyl, R⁷ is —C(=O)—OH, R² is F, and X is O.

In one particular embodiment, the present invention comprises a highly efficient process for making a compound of formula (I):

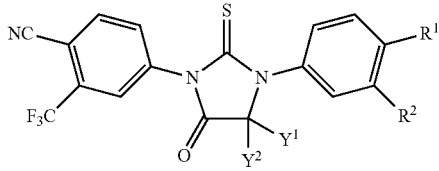

I wherein:
Y¹ and Y² are independently methyl or, together with the carbon to which they are attached, form a cycloalkyl group of 4 to 5 carbon atoms;
R¹ is L¹-C(=O)—NR⁴R⁵, or L¹-CN; where L¹ is a single bond or $C_1$-$C_8$ alkylene; and R⁴ and R⁵ are independently selected from H and $C_1$-$C_8$ alkyl; and
R² is hydrogen or fluoro;
said process comprising the following steps:
reacting a compound of formula A:

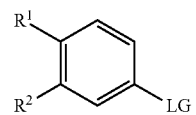

A wherein LG is Br, I or another good leaving group, with a compound of formula B:

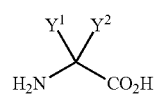

B to form a compound of formula C:

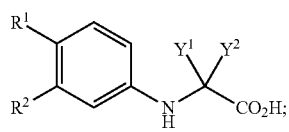

C reacting the compound of formula C with a compound of the formula R⁶—OH under conditions for esterification, or alternatively reacting the compound of formula C with a compound of the formula R⁶-LG, where R⁶ is $C_1$-$C_8$ alkyl and LG is Br, I, or another good leaving group, to form a compound of the formula D:

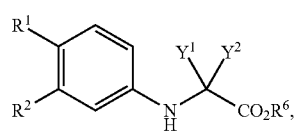

D reacting the compound of formula D with the compound of formula F, 4-isothiocyanato-2-(trifluoromethyl)benzonitrile,

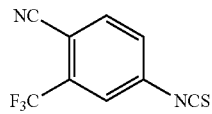

F to form the compound of formula (I):

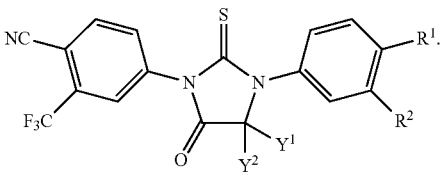

I

In one embodiment, with respect to the compounds of formula A, LG is Br or I. In a particular embodiment, LG is Br.

In one particular embodiment, the present invention comprises a highly efficient process for making a compound of formula (I):

*[Structure I: diarylthiohydantoin with NC, F$_3$C-phenyl on one N; R$^1$, R$^2$-phenyl on other N; Y$^1$, Y$^2$ substituents; C=O and C=S]*

I wherein:

Y$^1$ and Y$^2$ are independently methyl or, together with the carbon to which they are attached, form a cycloalkyl group of 4 to 5 carbon atoms;

R$^1$ is L$^1$-C(=O)—NR$^4$R$^5$, or L$^1$-CN; where L$^1$ is a single bond or C$_1$-C$_8$ alkylene; and R$^4$ and R$^5$ are independently selected from H and C$_1$-C$_8$ alkyl; and R$^2$ is hydrogen or fluoro;

said process comprising reacting the compound of formula A:

*[Structure A: R$^1$, R$^2$-substituted phenyl-Br]*

A with the compound of formula B:

*[Structure B: H$_2$N-C(Y$^1$)(Y$^2$)-CO$_2$H]*

B to yield a compound of formula C:

*[Structure C: R$^1$,R$^2$-phenyl-NH-C(Y$^1$)(Y$^2$)-CO$_2$H]*

C reacting the compound of formula C with a compound of formula E:

*[Structure E: NC, F$_3$C-substituted phenyl-NH$_2$]*

E to form the compound of formula G:

*[Structure G: NC, F$_3$C-phenyl-NH-C(=O)-C(Y$^1$)(Y$^2$)-NH-phenyl-R$^1$,R$^2$]*

G and reacting the compound of formula G with thiophosgene:

to yield the diarylthiohydantoin compound of formula (I):

*[Structure I: same as above]*

I

In one particular embodiment, with respect to the compound of formulae I, or I, 2-I, Y$^1$ and Y$^2$ are both methyl.

In one particular embodiment, with respect to the compound of formulae I, or I, 2-I, Y$^1$ and Y$^2$ together with the carbon to which they are attached combine to form a cyclobutyl ring In one particular embodiment, with respect to the compound of formulae I, or I, 2-I, Y$^1$ and Y$^2$ together with the carbon to which they are attached combine to form a cyclopentyl ring.

In one particular embodiment, with respect to the compound of formulae I, or I, 2-I, L$^1$ is a single bond.

In one particular embodiment, with respect to the compound of formulae I, or I, 2-I, L$^1$ is —CH$_2$—, —CH$_2$—CH$_2$—, or CH$_2$—CH$_2$—CH$_2$—.

In one particular embodiment, with respect to the compound of formulae I, or I, 2-I, L$^1$ is a single bond; and R$^1$ is —C(=O)—NHCH$_3$.

In one particular embodiment, with respect to the compound of formulae I, or I, 2-I, L$^1$ is a single bond; and R$^1$ is —C(=O)—NH$_2$.

In one particular embodiment, with respect to the compound of formulae I, or I, 2-I, R$^2$ is F.

In one particular embodiment, with respect to the compound of formulae I, or I, 2-I, Y$^1$ and Y$^2$ are both methyl, R$^1$ is —C(=O)—NHCH$_3$, and R$^2$ is F.

In one particular embodiment, with respect to the compound of formulae I, or I, 2-I, Y$^1$ and Y$^2$ are both methyl, R$^1$ is —C(=O)—NH$_2$, and R$^2$ is F.

In one particular embodiment, with respect to the compound of formulae I, or I, 2-I, the compound is according to formula II:

*[Structure II: diarylthiohydantoin with NC, F$_3$C-phenyl on one N; 2-fluoro-4-(C(=O)NHMe)-phenyl on other N; gem-dimethyl at 5-position]*

II

The overall scheme for one embodiment of the reaction, illustrated in the pathway proceeding A→C→D→I below, is summarized below in Scheme 1:

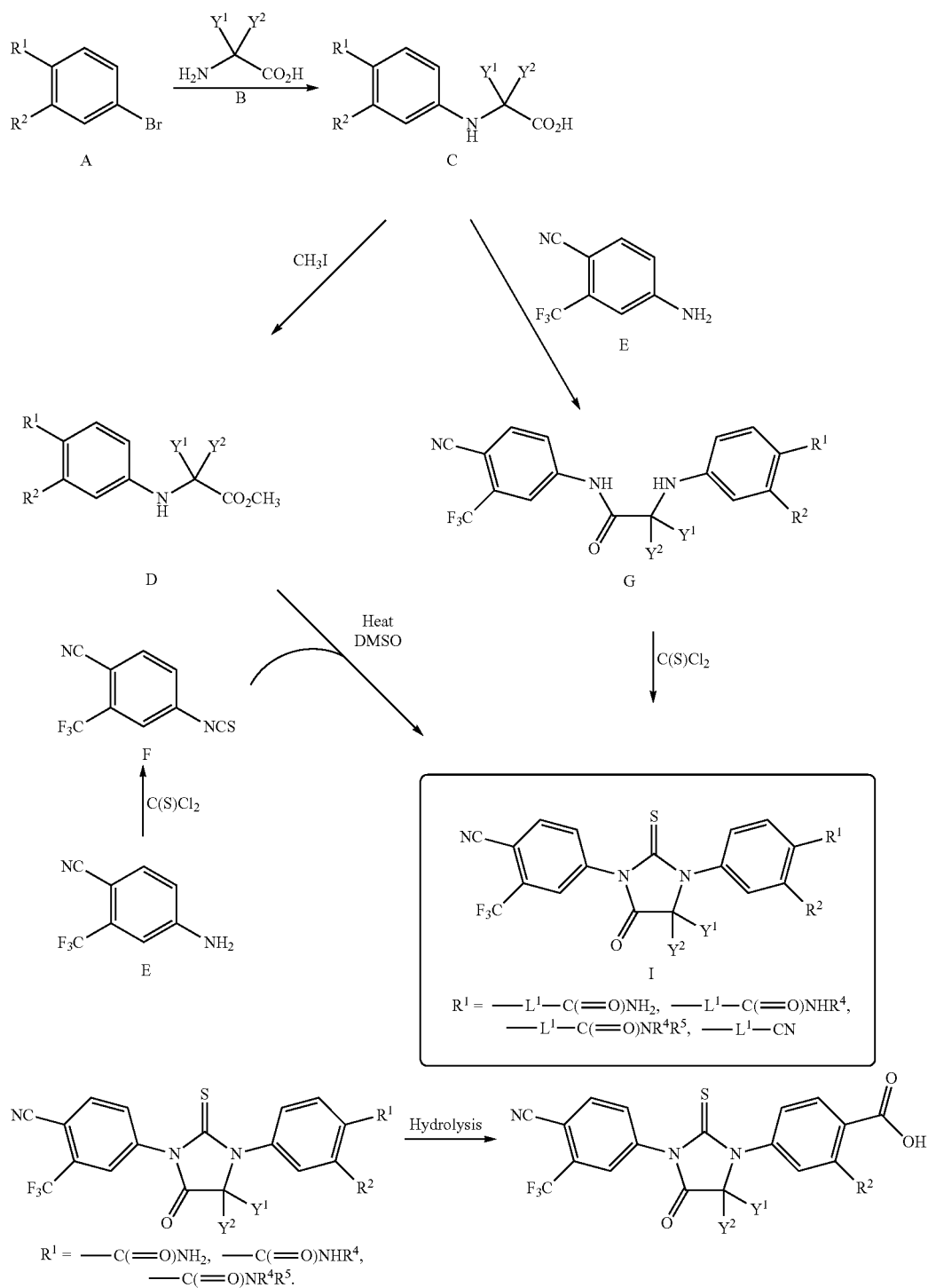

Scheme 1 where a) an optional synthesis of a) compound F from 4-amino-2-(trifluoromethyl)benzonitrile (compound E) and thiophosgene, and b) optional hydrolysis of the $R^1$ substituent of compound I to a carboxylic acid group, for synthesis when a carboxylic acid is desired in the $R^1$ position, are illustrated. In the optional hydrolysis of the $R^1$ substituent of compound I to a carboxylic acid group, $R^1$ is limited to -$L^1$-(C=O)NH$_2$, -$L^1$-(C=O)NHR$^4$, and -$L^1$-(C=O)NR$^4$R$^5$, as hydrolysis of $R^1$ when $R^1$ is -$L^1$-CN would result in hydrolysis of the other nitrile group present on the other benzene ring. In the hydrolysis depicted in Scheme 1, $L^1$ is a nonentity (i.e., a single bond) as hydrolysis is depicted as resulting in a —COOH group, but in other embodiments, $L^1$ can also be $C_1$-$C_8$ alkylene.

In an alternate procedure, the compound of formula C is treated with compound E, under amide bond-forming conditions to give the compound of formula G, which is followed by treatment with a reagent such as thiophosgene to form the compound of formula I (that is, the path C→G→I in the scheme above).

In one embodiment, a compound of formula A is mixed with a compound of formula B in the presence of a catalytic amount of both a copper (I) catalyst and a beta-dione ligand such as 2-acetylcyclohexanone, in a polar solvent and with heating to a temperature of about 90-120° C., about 100-110° C. or about 105° C. The copper (I) catalyst can be copper (I) chloride or copper (I) iodide. The copper (I) catalyst, such as CuCl, can be present in an amount of about 0.05-0.35 equivalents with respect to compound A, about 0.15-0.25 equivalents with respect to compound A, or about 0.2 equivalents with respect to compound A. The ligand, such as 2-acetylcyclohexanone, can be present in an amount of about 0.05-0.35 equivalents with respect to compound A, about 0.15-0.25 equivalents with respect to compound A, or about 0.2 equivalents with respect to compound A. In another embodiment, the ligand, such as 2-acetylcyclohexanone, is present in an amount about equal to the amount of copper (I) catalyst, such as copper (I) chloride, used. Compound B can be added in an amount of about 1-2 equivalents with respect to compound A, about 1.25-1.75 equivalents with respect to compound A, or about 1.5 equivalents with respect to compound A. A choice of beta-dione ligands will be known to those skilled in the art, such as 2,4-pentanedione, 2,4-hexanedione, 1-phenyl-1,3-butanedione, 2-acetylcyclohexanone, and the like. The polar solvent can be selected from the group consisting of dimethylsulfoxide (DMSO), dimethylformamide (DMF), N-methylpyrrolidone (NMP), dimethylacetamide (DMA), isopropylacetate (IPAc), isopropyl alcohol (IPA), and the like; in another embodiment, the polar solvent is DMF, water, or a mixture of DMF and water. In another embodiment, after reacting for about 6-24 h, about 8-20 h, or about 12-14 h, or after analysis shows about 90% or more of compound A has been consumed, the reaction mixture is then cooled to about 15-25° C., such as to about 25° C. or to room temperature. In another embodiment, water is added to the cooled reaction mixture followed by washing with a water-immiscible organic solvent such as isopropyl acetate; the mixture is then separated into organic and aqueous layers. In another embodiment, the aqueous layer is acidified to isolate compound C by precipitation, filtration and drying.

In one embodiment, the compound C is reacted with an alkylating agent of formula $R^6$-LG, where $R^6$ is $C_1$-$C_8$ alkyl and LG is Br, I, or another good leaving group, to form the compound of formula D. Compounds of formula $R^6$-LG include compounds such as methyl iodide. The reaction can be conducted in the presence of an inorganic base, such as $K_2CO_3$, $KHCO_3$, $Na_2CO_3$, or $NaHCO_3$, in a polar solvent, such as DMSO, DMF, NMP, DMA, or IPAc, and with a catalytic amount of water. The catalytic amount of water can be about 5-25%, 10-20%, or 14% of the equivalents of compound C, or about 0.05-0.25%, 0.10-0.20%, or 0.14% of the volume of the polar solvent. The reaction mixture can be heated to about 35-50° C. or about 40-46° C., for about 5-60 min, or until analysis shows greater than about 90% or about 95% or about 99% conversion of compound C to compound D. After reaction, the mixture can be cooled to about 5-25° C. or about 15-25° C. The reaction mixture containing compound D can be combined with water to precipitate the product D from solution. Product D can be isolated by filtration and drying. In one embodiment, the amount of inorganic base used, such as $K_2CO_3$, is about 2 equivalents or less than about 2 equivalents relative to compound C. In another embodiment, the amount of inorganic base used, such as $K_2CO_3$, is about 1.5 equivalents or less than about 1.5 equivalents relative to compound C. In another embodiment, the amount of inorganic base used, such as $K_2CO_3$, is about 1.2 equivalents or less than about 1.2 equivalents relative to compound C. In another embodiment, the amount of inorganic base used, such as $K_2CO_3$, is about 1.1 equivalents or less than about 1.1 equivalents relative to compound C. In another embodiment, the amount of inorganic base used, such as $K_2CO_3$, is about 1.0 equivalents or less than about 1.0 equivalents relative to compound C. In another embodiment, the amount of inorganic base used, such as $K_2CO_3$, is about 0.9 equivalents or less than about 0.9 equivalents relative to compound C. In another embodiment, the amount of inorganic base used, such as $K_2CO_3$, is about 0.8 equivalents or less than about 0.8 equivalents relative to compound C. In another embodiment, the amount of inorganic base used, such as $K_2CO_3$, is about 0.7 equivalents or less than about 0.7 equivalents relative to compound C. In another embodiment, the amount of inorganic base used, such as $K_2CO_3$, is about 0.6 equivalents or less than about 0.6 equivalents relative to compound C.

In another embodiment, when $CH_3I$ is used to generate D (where $R^6$=$CH_3$) excess $CH_3I$ is quenched with acetic acid. $CH_3I$ can be used in about 1-1.5 equivalents relative to compound C, such as in an amount of about 1.2 equivalents relative to compound C, and an amount of AcOH can be added in about the amount of, or slightly more than, the excess amount of methyl iodide (for example, when 1.2 equivalents of methyl iodide are used, where methyl iodide is used in 0.2 equivalent excess relative to compound C, then about 0.21-0.25 equivalents, or about 0.23 equivalents, of AcOH relative to compound C can be used) to quench unreacted $CH_3I$. Alternative methylating agents known to those skilled in the art, such as dimethylsulfate, can also be utilized for this step.

In another embodiment, the step of combining the reaction mixture containing compound D with water is carried out by gradually adding water to the warm reaction mixture over a time of about 0.5 hours to about 3.5 hours, about 0.6 hours to 3.4 hours, about 1 hours to 2 hours, or over a time of about 0.5, 0.6, 1, 2, 3, 3.4, or 3.5 hours, until about 1-5 volumes of water, or about 1-3 volumes of water, or about 2 volumes of water have been added (relative to the volume of the original reaction mixture), in order to precipitate compound D in a slower manner and reduce the amount of inorganic cation and base, such as K+, and $CO_3^{2-}$ from the inorganic base, such as $K_2CO_3$, that is used in the reaction. In one embodiment, the added water is at a temperature of about 50° C. to about 80° C., about 50° C. to about 70° C., about 55° C. to about 75° C., about 55° C. to about 65° C., about 57° C. to about 63° C., about 48° C. to about 53° C., or about 68° C. to about 71° C., or about 57° C., or about 70° C. In another embodiment, the precipitated compound D is re-suspended or re-slurried in water, and then the water is removed by filtration, in order to further reduce the amount of inorganic cation present. In another embodiment, the volume of water for re-suspension or re-slurry is about 5-15 volumes, or about 10 volumes. In another embodiment, the re-suspension or re-slurry is carried out for about 0.5 hours to about 3 hours, about 1.0 to about 2.0 hours, about 1.0 hour, about 1.5 hours, or about 2 hours. In another embodiment, the temperature of the re-suspension or re-slurry water is about 15° C. to about 35° C., about 20° C. to about 30° C., about 20° C. to about 25° C., or about 20° C. to about 23 hi Va ° C.

In another embodiment, the residual amount of inorganic cation, such as potassium ion, remaining in compound D is less than or equal to about 1000 parts per million (ppm). In another embodiment, the residual amount of inorganic cation, such as potassium ion, remaining in compound D is less than or equal to about 500 ppm. In another embodiment, the residual amount of inorganic cation, such as potassium ion, remaining in compound D is less than or equal to about 300 ppm.

In one embodiment, the residual amount of base, such as bicarbonate ion, carbonate ion, or other base, remaining in compound D is less than or equal to about 1000 parts per million (ppm). In another embodiment, the residual amount of base remaining in compound D is less than or equal to about 500 ppm. In another embodiment, the residual amount of base remaining in compound D is less than or equal to about 300 ppm.

In one embodiment, compound D can be dried by blowing or sucking dry air, dry nitrogen or argon, or other dry inert gas, over the compound. In another embodiment, compound D can be dried by placing the compound under vacuum (such as under about 1 mmHg vacuum or less, 0.5 mmHg vacuum or less, or 0.1 mmHg vacuum or less). In one embodiment, the residual amount of water remaining in compound D is less than or equal to about 0.5%. In one embodiment, the residual amount of water remaining in compound D is less than or equal to about 0.3%. In one embodiment, the residual amount of water remaining in compound D is less than or equal to about 0.1%. In one embodiment, the residual amount of water remaining in compound D is less than or equal to about 500 ppm. In one embodiment, the residual amount of water remaining in compound D is less than or equal to about 300 ppm. In one embodiment, the residual amount of water remaining in compound D is less than or equal to about 100 ppm.

An alternative method for formation of compound D from compound C utilizes standard Fischer esterification conditions comprising mixing compound C in methanol and heating for about 1-16 h at about 40-100° C. (or at reflux) with a catalytic amount of acid, such as one to five drops of sulfuric acid, hydrochloric acid, nitric acid, phosphoric acid or other mineral acid, p-toluenesulfonic acid, or sulfonic-acid-containing ion exchange resin; in one embodiment, $H_2SO_4$ is used. Water can be removed by azeotropic distillation (such as by a Dean-Stark trap) in some embodiments. After esterification is complete (about 70%, about 80%, about 90%, about 95%, or about 99% completion), isolation of compound D can be performed as described above.

In another embodiment of the invention, the step of forming of compound I comprises mixing compound D with compound F in a polar solvent, or a mixture of a first polar solvent and a second polar solvent, and heating to about 60-100° C., about 80-100° C., or about 80-85° C., for a time of about 1-48 h or about 12-24 h. In another embodiment, after reaction, the process continues by cooling the reaction mixture to about 15-30° C., to about 25° C., or to room temperature, and combining with water, followed by extracting the desired product with a polar solvent, or a mixture of a third polar solvent and a fourth polar solvent. Compound F can be added in an amount of about 1-3 equivalents with respect to compound D, or about 1.5-2.5 equivalents with respect to compound D, or about 1.5 equivalents or about 2 equivalents with respect to compound D, or in an amount of about 1.5 equivalents, followed by an additional portion of about 0.5 equivalents as the reaction progresses. The combined organic extract layer can be reduced in volume and seeded with crystals of the desired product I to commence crystallization upon cooling to about 0-10° C. or about 3-6° C., followed by isolating the crystalline product by filtration, and then drying the product by streaming air over the product or in vacuo. In one aspect of this embodiment, the polar solvent, or the first, second, third and fourth polar solvents, can be selected from the group consisting of DMSO, DMF, NMP, DMA, IPAc, MeCN, IPA, and the like. In one embodiment, the polar solvent is DMF. In one embodiment, the polar solvent is IPAc. In another embodiment, the first polar solvent is IPAc, and the second polar solvent is DMSO. In another embodiment, the third polar solvent is IPAc, and the fourth polar solvent is IPA. In another embodiment, the first polar solvent is IPAc, the second polar solvent is DMSO, the third polar solvent is IPAc, and the fourth polar solvent is IPA.

In another embodiment of the invention, an alternative method for the formation of compound I involves two steps, outlined in the pathway the path C→G→I in the scheme above. The first step utilizes standard amide-bond formation conditions, comprising for example treating compound C with a coupling reagent such as dicyclohexylcarbodiimide (DCC), diisopropylcarbodiimide (DIC), 1-ethyl-3-(3-dimethylaminopropyl)carbodiimide (EDCI), benzotriazol-1-yloxytris(dimethylamino)phosphonium hexafluorophosphate (BOP), 7-azabenzotriazol-1-yloxytris(dimethylamino)phosphonium hexafluorophosphate (AOP), benzotriazol-1-yloxytris(pyrrolidine)phosphonium hexafluorophosphate (PyBOP), 7-azabenzotriazol-1-yloxytris(pyrrolidine)phosphonium hexafluorophosphate (PyAOP), O-benzotriazole-N, N,N',N'-tetramethyluronium hexafluorophosphate (HBTU), O-(benzotriazol-1-yl)-N,N,N',N'-tetramethyluronium tetrafluoroborate (TBTU), O-(7-azabenzotriazol-1-yl)-N,N,N', N'-tetramethyluronium hexafluorophosphate (HATU), O-(7-azabenzotriazole-1-yl)-N,N,N',N'-tetramethyluronium tetrafluoroborate (TATU), and the like, with compound E, in a polar solvent or a mixture of a first polar solvent and a second polar solvent to give compound G. In one aspect of this embodiment, the polar solvent is, or the first and second polar solvents are, selected from the group consisting of DCM, DMSO, DMF, NMP, DMA, MeCN, and the like. The second step comprises a ring-closure reaction of compound G with a thiocarbonylation reagent such as thiophosgene, and heating the neat solution to about 60-120° C. In another embodiment, the reaction is performed in a sealed-tube apparatus. Thiophosgene or a thiophosgene equivalent (for example, 1,1-thiocarbonyl diimidazole) can be present in an amount of about 1-10 equivalents with respect to compound G, or about 5 equivalents with respect to compound G.

In another embodiment of the invention, compound I can be subjected to hydrolytic conditions when $R^1$ is a primary or secondary amide group, to produce the corresponding carboxylic acid derivative.

In one embodiment of the above method, substituent $R^1$ of the compound of formula A is —C(=O)—NH—$R^4$. In another embodiment, $R^1$ is —C(=O)—NH—$CH_3$. In another embodiment, substituent $R^2$ of the compound of formula A is fluorine. In another embodiment, $R^1$ is —C(=O)—NH—$R^4$ and $R^2$ is fluorine. In another embodiment, $R^1$ is —C(=O)—NH—$CH_3$ and $R^2$ is fluorine, and the compound of formula A is 4-bromo-2-fluoro-N-methylbenzamide.

In one embodiment of the above method, the compound of formula B is 2-aminoisobutyric acid (i.e., $Y^1$ and $Y^2$ are each $CH_3$). In another embodiment of the above method, the compound of formula B is 1-aminocyclobutanecarboxylic acid. In another embodiment of the above method, the compound of formula B is 1-aminocyclopentanecarboxylic acid.

In another embodiment, $Y^1$ and $Y^2$ are each $CH_3$, $R^1$ is —C(=O)$NHCH_3$ and/or $R^2$ is F.

In another embodiment, $Y^1$ and $Y^2$ are each $CH_3$, $R^1$ is —C(=O)$NH_2$ and/or $R^2$ is F.

Variations of the compound of formula (I) are also provided. Compounds of formula (I) or a variation thereof as detailed herein or a pharmaceutically acceptable salt of any of the foregoing may find particular use in the treatment of prostate cancer, including CRPC and/or hormone-sensitive prostate cancer.

In an alternate embodiment of the synthesis of compounds of I, 2-Ia, where $R^7$ is —C(=O)OH, the final product can be synthesized as follows (illustrated using the isothiocyanate):

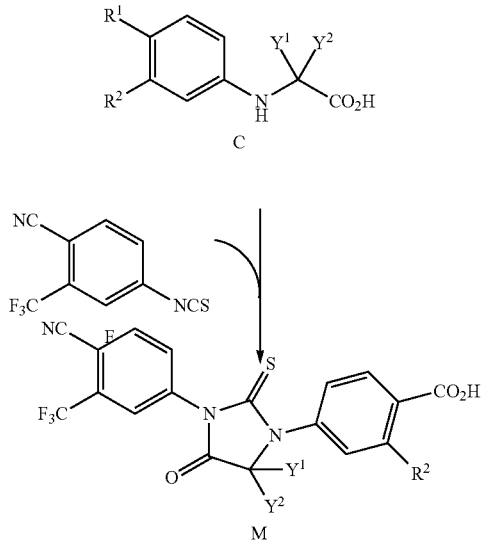

where compound C is reacted with compound F (4-isothiocyanato-2-(trifluoromethyl)benzonitrile) to form product M. In one embodiment, $Y^1$ and $Y^2$ are each $CH_3$, and/or $R^2$ is F. The reaction can be run under basic conditions, with a trialkylamino base such as triethylamine present in about 2-5 equivalents, or about 3-4 equivalents, or about 3.4 equivalents, relative to compound C. Compound F, 4-isothiocyanato-2-(trifluoromethyl)benzonitrile, can be present in amounts of about 1.1-4 equivalents, or 1.1-2 equivalents, or about 1.5 equivalents, relative to compound C; alternatively, about 1.5 equivalents of compound F can be added, followed by another portion of about 0.5 equivalents as the reaction progresses. The solvent can be ethanol or another alcohol. The reaction mixture can be stirred for about 4-16 days, about 8-12 days, or about 10 days, at room temperature or elevated temperature. Afterwards, the reaction mixture can be concentrated, mixed with aqueous acid such as 1M HCl, and the product extracted with an organic solvent, such as ethyl acetate, to obtain the product M.

In an additional embodiment, the compound C is synthesized by reacting a compound of formula J with a 1,1-disubstituted 2,2,2-trichloroethanol:

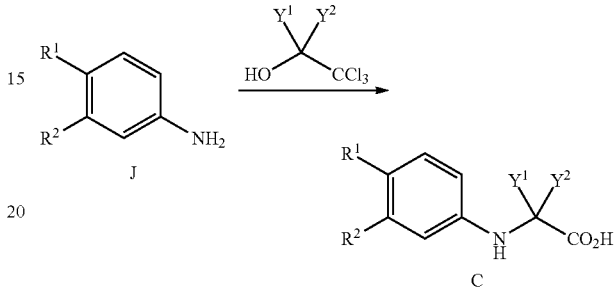

where the 1,1-disubstituted 2,2,2-trichloroethanol can be used in about 1.5-4 equivalents relative to J, or about 2-3 equivalents relative to J, about 2.5 equivalents relative to J, or about 2.6 equivalents relative to J. The reaction is carried out in an organic solvent, preferably an anhydrous solvent, such as anhydrous acetone. The reaction can be cooled to 0° C. prior to addition of a strong base, such as NaOH, KOH, or other hydroxide. The base is added in about 2-5 equivalents, or about 3-4 equivalents, or about 3.8 equivalents, or about 3.9 equivalents, relative to J. After addition of base, the reaction can be allowed to warm to room temperature, and is left at room temperature for about 4-24 h, or about 8-16 h, or about 12 h. The product can be purified by standard methods, such as column chromatography or HPLC.

In another embodiment, the invention embraces methods of making hydantoin compounds according to Scheme 2:

Scheme 2

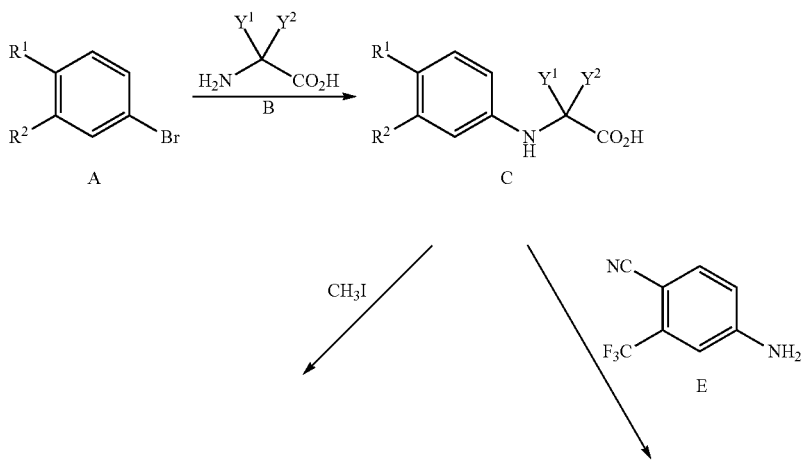

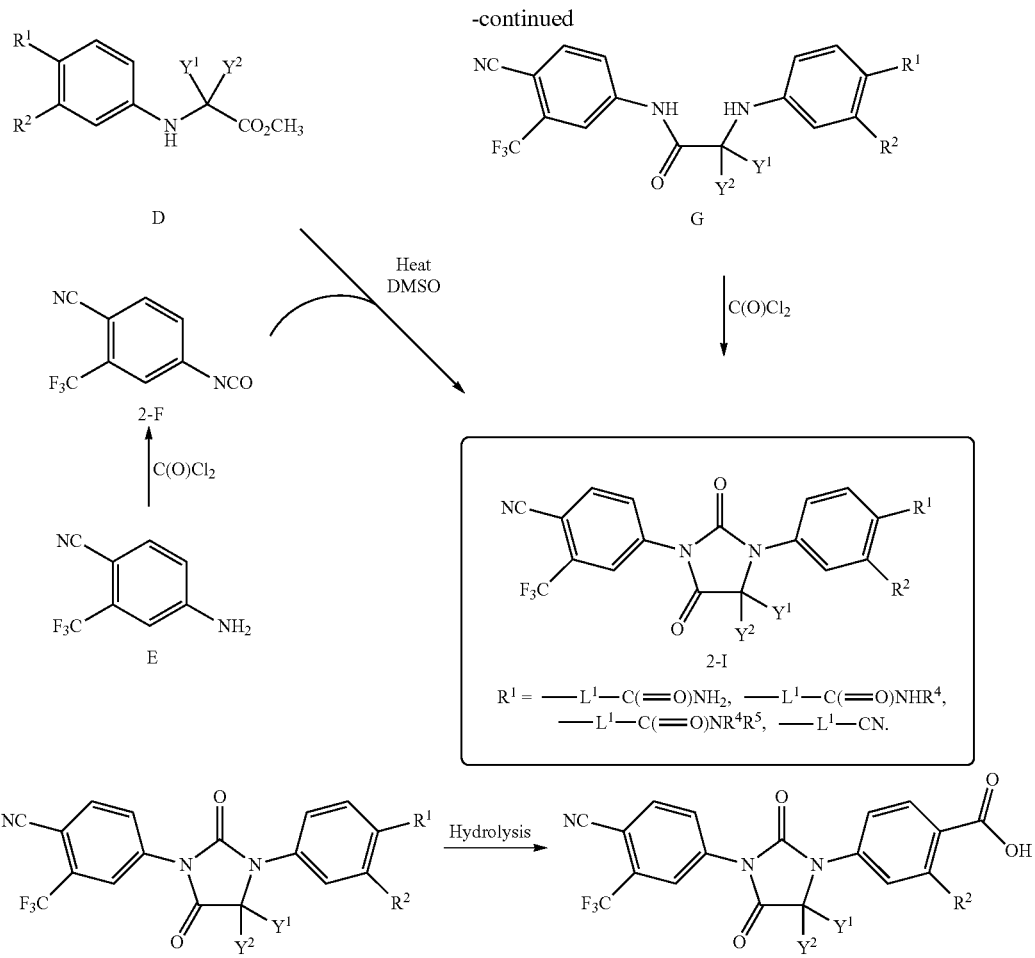

where $R^1 = -L^1-(C=O)NH_2$, $-L^1-(C=O)NHR^4$, $-L^1-(C=O)NR^4R^5$, or $L^1$-CN for compound 2-I. The reactions are analogous to those in Scheme 1, with replacement of thiophosgene with phosgene and replacement of the thioisocyanate F with isocyanate 2-F, resulting in the product hydantoin 2-I instead of the thiohydantoin I. It should be noted that phosgene can be replaced with phosgene equivalents such as 1,1-carbonyl diimidazole (see, e.g., the reagents described in *Phosgenations—A Handbook*, by Livius Cotarca and Heiner Eckert, Weinheim, Germany: Wiley-VCH Verlag GmbH & Co., 2003, particularly the phosgene equivalents listed in Chapter 3). Analogously to Scheme 1, an optional synthesis of a) compound 2-F from 4-amino-2-(trifluoromethyl)benzonitrile (compound E) and phosgene, and b) optional hydrolysis of the $R^1$ substituent of compound 2-I to a carboxylic acid group, for synthesis when a carboxylic acid is desired in the $R^1$ position, are illustrated. In the optional hydrolysis of the $R^1$ substituent of compound 2-I to a carboxylic acid group, $R^1$ is limited to $-L^1-(C=O)NH_2$, $-L^1-(C=O)NHR^4$, and $-L^1-(C=O)NR^4R^5$, as hydrolysis of $R^1$ when $R^1$ is $-L^1$-CN would result in hydrolysis of the other nitrile group present on the other benzene ring. In the hydrolysis depicted in Scheme 2, $L^1$ is a nonentity (i.e., a single bond) as hydrolysis is depicted as resulting in a —COOH group, but in other embodiments, $L^1$ can also be $C_1$-$C_8$ alkylene.

In the hydantoin embodiment, the present invention comprises a highly efficient process for making a compound of formula (2-I):

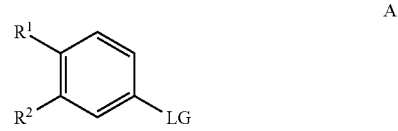

2-I wherein:
$Y^1$ and $Y^2$ are independently methyl or, together with the carbon to which they are attached, form a cycloalkyl group of 4 to 5 carbon atoms;
$R^1$ is $L^1$-C(=O)—$NR^4R^5$, or $L^1$-CN; where $L^1$ is a single bond or $C_1$-$C_8$ alkylene; and
$R^4$ and $R^5$ are independently selected from H and $C_1$-$C_8$ alkyl; and
$R^2$ is hydrogen or fluoro;
said process comprising the following steps:
reacting a compound of formula A:

A wherein LG is Br, I or another good leaving group, with a compound of formula B:

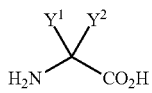

to form a compound of formula C:

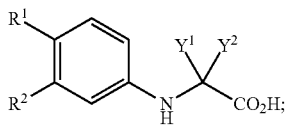

reacting the compound of formula C with a compound of the formula $R^6$—OH under conditions for esterification, or alternatively reacting the compound of formula C with a compound of the formula $R^6$-LG, where $R^6$ is $C_1$-$C_8$ alkyl and LG is Br, I, or another good leaving group, to form a compound of the formula D:

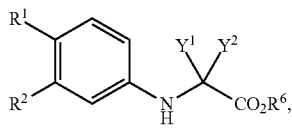

reacting the compound of formula D with the compound of formula 2-F, 4-isocyanato-2-(trifluoromethyl)benzonitrile,

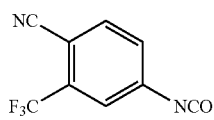

to form the compound of formula (2-I):

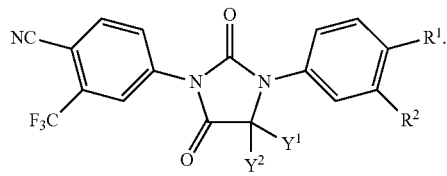

The overall scheme for this embodiment of the reaction is illustrated in the pathway proceeding A→C→D→2-I in Scheme 2.

In an alternate embodiment, the present invention comprises a highly efficient process for making a compound of formula (2-I):

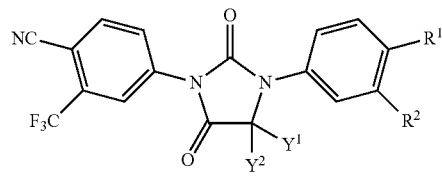

wherein:
$Y^1$ and $Y^2$ are independently methyl or, together with the carbon to which they are attached, form a cycloalkyl group of 4 to 5 carbon atoms;
$R^1$ is $L^1$-C(=O)—$NR^4R^5$, or $L^1$-CN; where $L^1$ is a single bond or $C_1$-$C_8$ alkylene; and
$R^4$ and $R^5$ are independently selected from H and $C_1$-$C_8$ alkyl; and
$R^2$ is hydrogen or fluoro;
said process comprising reacting the compound of formula A:

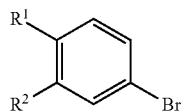

with the compound of formula B:

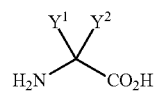

to yield a compound of formula C:

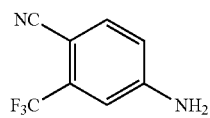

reacting the compound of formula C with a compound of formula E:

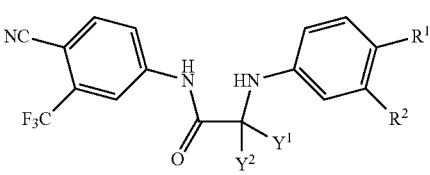

to form the compound of formula G:

and reacting the compound of formula G with phosgene: to yield the diarylhydantoin compound of formula (2-I):

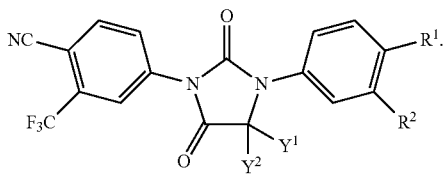

In this alternate embodiment, the compound of formula C is treated with compound E, under amide bond-forming conditions to give the compound of formula G, which is followed by treatment with a reagent such as phosgene to form the compound of formula 2-I (that is, the path C→G→2-I in Scheme 2).

In one embodiment, a compound of formula A is mixed with a compound of formula B in the presence of a catalytic amount of both a copper (I) catalyst and a beta-dione ligand such as 2-acetylcyclohexanone, in a polar solvent and with heating to a temperature of about 90-120° C., about 100-110° C. or about 105° C. The copper (I) catalyst can be copper (I) chloride or copper (I) iodide. The copper (I) catalyst, such as CuCl, can be present in an amount of about 0.05-0.35 equivalents with respect to compound A, about 0.15-0.25 equivalents with respect to compound A, or about 0.2 equivalents with respect to compound A. The ligand, such as 2-acetylcyclohexanone, can be present in an amount of about 0.05-0.35 equivalents with respect to compound A, about 0.15-0.25 equivalents with respect to compound A, or about 0.2 equivalents with respect to compound A. In another embodiment, the ligand, such as 2-acetylcyclohexanone, is present in an amount about equal to the amount of copper (I) catalyst, such as copper (I) chloride, used. Compound B can be added in an amount of about 1-2 equivalents with respect to compound A, about 1.25-1.75 equivalents with respect to compound A, or about 1.5 equivalents with respect to compound A. A choice of beta-dione ligands will be known to those skilled in the art, such as 2,4-pentanedione, 2,4-hexanedione, 1-phenyl-1,3-butanedione, 2-acetylcyclohexanone, and the like. The polar solvent can be selected from the group consisting of dimethylsulfoxide (DMSO), dimethylformamide (DMF), N-methylpyrrolidone (NMP), dimethylacetamide (DMA), isopropylacetate (IPAc), isopropyl alcohol (IPA), and the like; in another embodiment, the polar solvent is DMF, water, or a mixture of DMF and water. In another embodiment, after reacting for about 6-24 h, about 8-20 h, or about 12-14 h, or after analysis shows about 90% or more of compound A has been consumed, the reaction mixture is then cooled to about 15-25° C., such as to about 25° C. or to room temperature. In another embodiment, water is added to the cooled reaction mixture followed by washing with a water-immiscible organic solvent such as isopropyl acetate; the mixture is then separated into organic and aqueous layers. In another embodiment, the aqueous layer is acidified to isolate compound C by precipitation, filtration and drying.

In one embodiment, the compound C is reacted with an alkylating agent of formula $R^6$-LG, where $R^6$ is $C_1$-$C_8$ alkyl and LG is Br, I, or another good leaving group, to form the compound of formula D. Compounds of formula $R^6$-LG include compounds such as methyl iodide. The reaction can be conducted in the presence of an inorganic base, such as $K_2CO_3$, $KHCO_3$, $Na_2CO_3$, or $NaHCO_3$, in a polar solvent, such as DMSO, DMF, NMP, DMA, or IPAc, and with a catalytic amount of water. The catalytic amount of water can be about 5-25%, 10-20%, or 14% of the equivalents of compound C, or about 0.05-0.25%, 0.10-0.20%, or 0.14% of the volume of the polar solvent. The reaction mixture can be heated to about 35-50° C. or about 40-46° C., for about 5-60 min, or until analysis shows greater than about 90% or about 95% or about 99% conversion of compound C to compound D. After reaction, the mixture can be cooled to about 5-25° C. or about 15-25° C. The reaction mixture containing compound D can be combined with water to precipitate the product D from solution. Product D can be isolated by filtration and drying. In one embodiment, the amount of inorganic base used, such as $K_2CO_3$, is about 2 equivalents or less than about 2 equivalents relative to compound C. In another embodiment, the amount of inorganic base used, such as $K_2CO_3$, is about 1.5 equivalents or less than about 1.5 equivalents relative to compound C. In another embodiment, the amount of inorganic base used, such as $K_2CO_3$, is about 1.2 equivalents or less than about 1.2 equivalents relative to compound C.

In another embodiment, when $CH_3I$ is used to generate D (where $R^6$=$CH_3$) excess $CH_3I$ is quenched with acetic acid. $CH_3I$ can be used in about 1-1.5 equivalents relative to compound C, such as in an amount of about 1.2 equivalents relative to compound C, and an amount of AcOH can be added in about the amount of, or slightly more than, the excess amount of methyl iodide (for example, when 1.2 equivalents of methyl iodide are used, where methyl iodide is used in 0.2 equivalent excess relative to compound C, then about 0.21-0.25 equivalents, or about 0.23 equivalents, of AcOH relative to compound C can be used) to quench unreacted $CH_3I$. Alternative methylating agents known to those skilled in the art, such as dimethylsulfate, can also be utilized for this step.

In another embodiment, the step of combining the reaction mixture containing compound D with water is carried out by gradually adding water to the warm reaction mixture over 1-2 h, until about 1-5 volumes of water, or about 1-3 volumes of water, or about 2 volumes of water have been added (relative to the volume of the original reaction mixture), in order to precipitate compound D in a slower manner and reduce the amount of inorganic cation and base, such as $K^+$, and $CO_3^{2-}$ from the inorganic base, such as $K_2CO_3$, that is used in the reaction. In another embodiment, the precipitated compound D is re-suspended or re-slurried in water, and then the water is removed by filtration, in order to further reduce the amount of inorganic cation present.

In one embodiment, the residual amount of inorganic cation, such as potassium ion, remaining in compound D is less than or equal to about 1000 parts per million (ppm). In another embodiment, the residual amount of inorganic cation, such as potassium ion, remaining in compound D is less than or equal to about 500 ppm. In another embodiment, the residual amount of inorganic cation, such as potassium ion, remaining in compound D is less than or equal to about 300 ppm.

In one embodiment, the residual amount of base, such as bicarbonate ion, carbonate ion, or other base, remaining in compound D is less than or equal to about 1000 parts per million (ppm). In another embodiment, the residual amount of base remaining in compound D is less than or equal to about 500 ppm. In another embodiment, the residual amount of base remaining in compound D is less than or equal to about 300 ppm.

In one embodiment, compound D can be dried by blowing or sucking dry air, dry nitrogen or argon, or other dry inert gas, over the compound. In another embodiment, compound D can be dried by placing the compound under vacuum (such as under about 1 mmHg vacuum or less, 0.5 mmHg vacuum or less, or 0.1 mmHg vacuum or less). In one embodiment, the residual amount of water remaining in compound D is less than or equal to about 0.5%. In one embodiment, the residual amount of water remaining in compound D is less than or equal to about 0.3%. In one embodiment, the residual amount of water remaining in compound D is less than or equal to about 0.1%. In one embodiment, the residual amount of water remaining in compound D is less than or equal to about 500 ppm. In one embodiment, the residual amount of water remaining in compound D is less than or equal to about 300 ppm. In one embodiment, the residual amount of water remaining in compound D is less than or equal to about 100 ppm.

An alternative method for formation of compound D from compound C utilizes standard Fischer esterification conditions comprising mixing compound C in methanol and heating for about 1-16 h at about 40-100° C. (or at reflux) with a catalytic amount of acid, such as one to five drops of sulfuric acid, hydrochloric acid, nitric acid, phosphoric acid, or other mineral acid, p-toluenesulfonic acid, or sulfonic-acid-containing ion exchange resin; in one embodiment, $H_2SO_4$ is used. Water can be removed by azeotropic distillation (such as by a Dean-Stark trap) in some embodiments. After esterification is complete (about 70%, about 80%, about 90%, about 95%, or about 99% completion), isolation of compound D can be performed as described above.

In another embodiment of the invention, the step of forming of compound 2-I comprises mixing compound D with compound 2-F in a polar solvent, or a mixture of a first polar solvent and a second polar solvent, and heating to about 60-100° C., about 80-100° C., or about 80-85° C., for a time of about 1-48 h or about 12-24 h. In another embodiment, after reaction, the process continues by cooling the reaction mixture to about 15-30° C., to about 25° C., or to room temperature, and combining with water, followed by extracting the desired product with a polar solvent, or a mixture of a third polar solvent and a fourth polar solvent. Compound 2-F can be added in an amount of about 1-3 equivalents with respect to compound D, or about 1.5-2.5 equivalents with respect to compound D, or about 1.5 equivalents or about 2 equivalents with respect to compound D, or in an amount of about 1.5 equivalents, followed by an additional portion of about 0.5 equivalents as the reaction progresses. The combined organic extract layer can be reduced in volume and seeded with crystals of the desired product 2-I to commence crystallization upon cooling to about 0-10° C. or about 3-6° C., followed by isolating the crystalline product by filtration, and then drying the product by streaming air over the product or in vacuo. In one aspect of this embodiment, the polar solvent, or the first, second, third and fourth polar solvents, can be selected from the group consisting of DMSO, DMF, NMP, DMA, IPAc, MeCN, IPA, and the like. In one embodiment, the polar solvent is DMF. In another embodiment, the first polar solvent is IPAc, and the second polar solvent is DMSO. In another embodiment, the third polar solvent is IPAc, and the fourth polar solvent is IPA. In another embodiment, the first polar solvent is IPAc, the second polar solvent is DMSO, the third polar solvent is IPAc, and the fourth polar solvent is IPA.

In another embodiment of the invention, an alternative method for the formation of compound 2-I involves two steps, outlined in the pathway the path C→G→2-I in Scheme 2. The first step utilizes standard amide-bond formation conditions, comprising for example treating compound C with a coupling reagent such as dicyclohexylcarbodiimide (DCC), diisopropylcarbodiimide (DIC), 1-ethyl-3-(3-dimethylaminopropyl) carbodiimide (EDCI), benzotriazol-1-yloxytris(dimethylamino)phosphonium hexafluorophosphate (BOP), 7-azabenzotriazol-1-yloxytris(dimethylamino)phosphonium hexafluorophosphate (AOP), benzotriazol-1-yloxytris(pyrrolidine)phosphonium hexafluorophosphate (PyBOP), 7-azabenzotriazol-1-yloxytris(pyrrolidine)phosphonium hexafluorophosphate (PyAOP), O-benzotriazole-N,N,N',N'-tetramethyluronium hexafluorophosphate (HBTU), O-(benzotriazol-1-yl)-N,N,N',N'-tetramethyluronium tetrafluoroborate (TBTU), O-(7-azabenzotriazol-1-yl)-N,N,N',N'-tetramethyluronium hexafluorophosphate (HATU), O-(7-azabenzotriazole-1-yl)-N,N,N',N'-tetramethyluronium tetrafluoroborate (TATU), and the like, with compound E, in a polar solvent or a mixture of a first polar solvent and a second polar solvent to give compound G. In one aspect of this embodiment, the polar solvent is, or the first and second polar solvents are, selected from the group consisting of DCM, DMSO, DMF, NMP, DMA, MeCN, and the like. The second step comprises a ring-closure reaction of compound G with a carbonylation reagent such as phosgene, and heating the neat solution to about 60-120° C. In another embodiment, the reaction is performed in a sealed-tube apparatus. Phosgene or a phosgene equivalent (for example, carbonyl diimidazole) can be present in an amount of about 1-10 equivalents with respect to compound G, or about 5 equivalents with respect to compound G.

In another embodiment of the invention, compound 2-I can be subjected to hydrolytic conditions when $R^1$ is a primary or secondary amide group, to produce the corresponding carboxylic acid derivative.

In one embodiment of the above method, substituent $R^1$ of the compound of formula A is —C(=O)—NH—$R^4$. In another embodiment, $R^1$ is —C(=O)—NH—$CH_3$. In another embodiment, substituent $R^2$ of the compound of formula A is fluorine. In another embodiment, $R^1$ is —C(=O)—NH—$R^4$ and $R^2$ is fluorine. In another embodiment, $R^1$ is —C(=O)—NH—$CH_3$ and $R^2$ is fluorine, and the compound of formula A is 4-bromo-2-fluoro-N-methylbenzamide.

In one embodiment of the above method, the compound of formula B is 2-aminoisobutyric acid (i.e., $Y^1$ and $Y^2$ are each $CH_3$). In another embodiment of the above method, the compound of formula B is 1-aminocyclobutanecarboxylic acid. In another embodiment of the above method, the compound of formula B is 1-aminocyclopentanecarboxylic acid.

In another embodiment, $Y^1$ and $Y^2$ are each $CH_3$, $R^1$ is —C(=O)NH$CH_3$ and/or $R^2$ is F.

In another embodiment, $Y^1$ and $Y^2$ are each $CH_3$, $R^1$ is —C(=O)$NH_2$ and/or $R^2$ is F.

In another embodiment, $Y^1$ and $Y^2$ are each $CH_3$, $R^1$ is replaced by a —C(=O)OH group, and/or $R^2$ is F.

Variations of the compound of formula (2-I) are also provided. Compounds of formula (2-I) or a variation thereof as detailed herein or a pharmaceutically acceptable salt of any of the foregoing may find particular use in the treatment of prostate cancer, including CRPC and/or hormone-sensitive prostate cancer.

In an alternate embodiment, where a —C(=O)OH group replaced the $R^1$ group, the final product can be synthesized as follows:

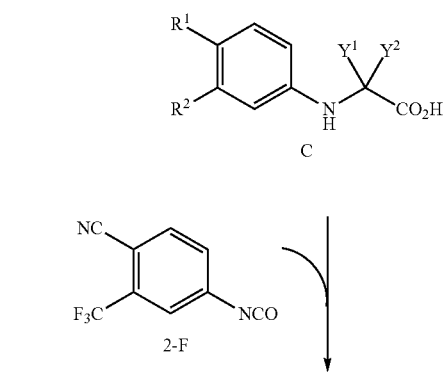

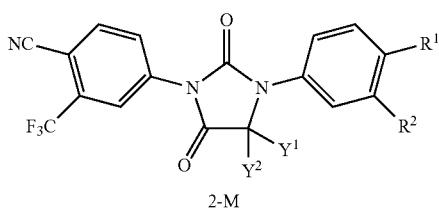

2-M

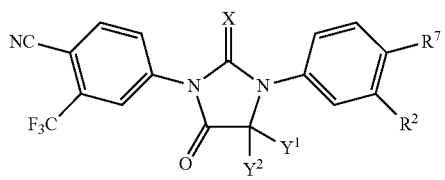

I, 2-Ia where compound C is reacted with compound 2-F (4-isocyanato-2-(trifluoromethyl)benzonitrile) to form product 2-M. The reaction can be run under basic conditions, with a trialkylamino base such as triethylamine present in about 2-5 equivalents, or about 3-4 equivalents, or about 3.4 equivalents, relative to compound C. Compound 2-F, 4-isocyanato-2-(trifluoromethyl)benzonitrile, can be present in amounts of about 1.1-4 equivalents, or 1.1-2 equivalents, or about 1.5 equivalents, relative to compound C; alternatively, about 1.5 equivalents of compound 2-F can be added, followed by another portion of about 0.5 equivalents as the reaction progresses. The solvent can be ethanol or another alcohol. The reaction mixture can be stirred for about 4-16 days, about 8-12 days, or about 10 days, at room temperature or elevated temperature. Afterwards, the reaction mixture can be concentrated, mixed with aqueous acid such as 1M HCl, and the product extracted with an organic solvent, such as ethyl acetate, to obtain the product 2-M.

In an additional embodiment, the compound C is synthesized by reacting a compound of formula J with a 1,1-disubstituted 2,2,2-trichloroethanol:

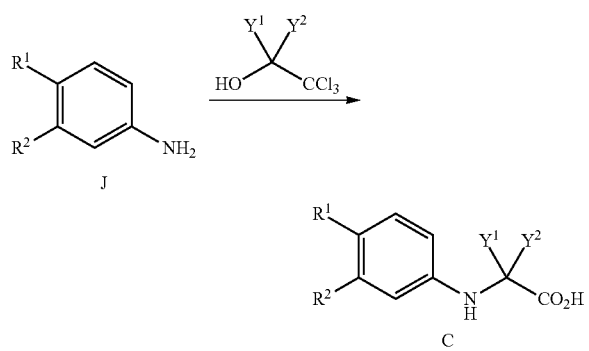

where the 1,1-disubstituted 2,2,2-trichloroethanol can be used in about 1.5-4 equivalents relative to J, or about 2-3 equivalents relative to J, about 2.5 equivalents relative to J, or about 2.6 equivalents relative to J. The reaction is carried out in an organic solvent, preferably an anhydrous solvent, such as anhydrous acetone. The reaction can be cooled to 0° C. prior to addition of a strong base, such as NaOH, KOH, or other hydroxide. The base is added in about 2-5 equivalents, or about 3-4 equivalents, or about 3.8 equivalents, or about 3.9 equivalents, relative to J. After addition of base, the reaction can be allowed to warm to room temperature, and is left at room temperature for about 4-24 h, or about 8-16 h, or about 12 h. The product can be purified by standard methods, such as column chromatography or HPLC.

In another embodiment, the invention embraces a process for preparing a compound of formula (I, 2-Ia):

wherein X is S or O; $Y^1$ and $Y^2$ are independently methyl or, together with the carbon to which they are attached, form a cycloalkyl group of 4 to 5 carbon atoms; $R^7$ is $L^1$-COOH, where $L^1$ is a single bond or $C_1$-$C_8$ alkylene; and $R^4$ and $R^5$ are independently selected from H and $C_1$-$C_8$ alkyl; and $R^2$ is hydrogen or fluoro; said process comprising reacting the compound of formula Aa:

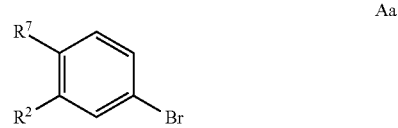

wherein LG is a leaving group, Br, or I; with the compound of formula B:

to yield a compound of formula Ca:

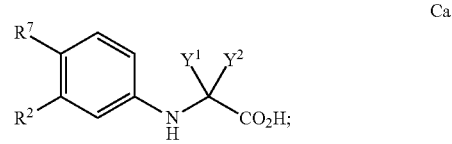

reacting the compound of formula Ca with a compound of formula $R^6$-LG under alkylating conditions or with a compound of formula $R^6$—OH under esterification conditions to form the compound of formula Da:

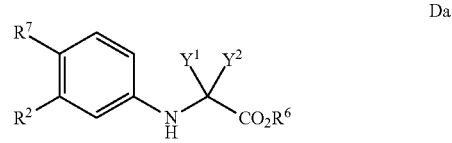

wherein $R^6$ is $C_1$-$C_8$ alkyl; and reacting the compound of formula Da with the compound of formula (F,2-F):

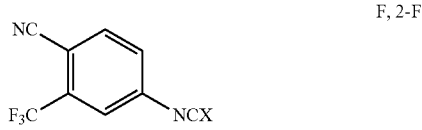

where X is S or O, to yield the diarylthiohydantoin or diarylhydantoin compound of formula (I, 2-Ia):

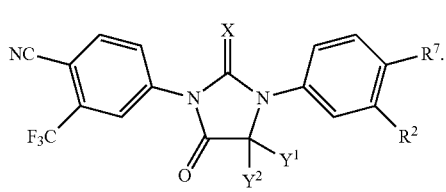

I, 2-Ia

In one embodiment, X is S. In another embodiment, X is O. In any of these embodiments, $L^1$ can be a single bond; and $R^7$ can —C(=O)—OH. In any of these embodiments, $Y^1$ and $Y^2$ can both be methyl, $R^7$ can be —C(=O)—OH, and $R^2$ can be F.

In another embodiment, pharmaceutical compositions of any of the compounds detailed herein are embraced by this invention. Thus, the invention includes pharmaceutical compositions comprising a compound described herein or a pharmaceutically acceptable salt thereof and a pharmaceutically acceptable carrier or excipient. Pharmaceutical compositions according to the invention may take a form suitable for oral, buccal, parenteral, subcutaneous, intramuscular, intravenous, nasal, topical or rectal administration, or a form suitable for administration by inhalation.

DETAILED DESCRIPTION OF THE INVENTION

Definitions

For use herein, unless clearly indicated otherwise, use of the terms "a", "an" and the like refers to one or more.

The term "about" as used herein refers to the usual range of variation for the respective value readily known to the skilled person in this technical field. Reference to "about" a value or parameter herein includes (and describes) embodiments that are directed to that value or parameter per se.

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion such as potassium or sodium, an alkaline earth ion such as calcium, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Further examples of pharmaceutically acceptable salts include those listed in Berge et al., Pharmaceutical Salts, J. Pharm. Sci. 1977 January; 66(1):1-19. Pharmaceutically acceptable salts can be prepared in situ in the manufacturing process, or by separately reacting a purified compound of the invention in its free acid or base form with a suitable organic or inorganic base or acid, respectively, and isolating the salt thus formed during subsequent purification. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

"Alkyl" refers to and includes saturated linear, branched, or cyclic hydrocarbon structures and combinations thereof. Particular alkyl groups are those having 1 to 12 carbon atoms (a "$C_1$-$C_{12}$ alkyl"). More particular alkyl groups are those having 1 to 8 carbon atoms (a "$C_1$-$C_8$ alkyl"). When an alkyl residue having a specific number of carbons is named, all geometric isomers having that number of carbons are intended to be encompassed and described; thus, for example, "butyl" is meant to include n-butyl, sec-butyl, iso-butyl, tert-butyl and cyclobutyl; "propyl" includes n-propyl, iso-propyl and cyclopropyl. This term is exemplified by groups such as methyl, t-butyl, n-heptyl, octyl, cyclohexylmethyl, cyclopropyl and the like. Cycloalkyl is a subset of alkyl and can consist of one ring, such as cyclohexyl, or multiple rings, such as adamantyl. A cycloalkyl comprising more than one ring may be fused, spiro or bridged, or combinations thereof. A preferred cycloalkyl has from 3 to 12 annular carbon atoms. A more preferred cycloalkyl has from 3 to 7 annular carbon atoms (a "$C_3$-$C_7$ cycloalkyl"). Examples of cycloalkyl groups include adamantyl, decahydronaphthalenyl, cyclopropyl, cyclobutyl, cyclopentyl and the like.

"Substituted alkyl" refers to an alkyl group having from 1 to 5 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Leaving Groups" are those groups which depart with a pair of electrons in heterolytic bond cleavage, such as occurs during nucleophilic substitution. Good leaving groups, include, for example: Cl, Br, I, triflates, diazonium salts, fluorosulfonates, tosylates, and mesylates. The particular leaving groups include Cl, Br, or I. More particular groups include Br, or I.

The features and effects of the present invention will be further explained with reference to the embodiments discussed below, which are, however, not intended to restrict the scope of the present invention.

Process

The present invention comprises a highly efficient process for manufacture of diarylthiohydantoin compounds of formula (I):

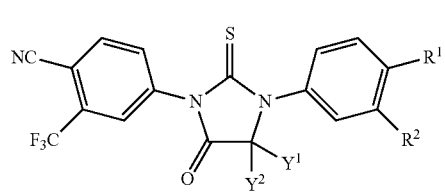

wherein:

$Y^1$ and $Y^2$ are independently methyl or, together with the carbon to which they are attached, form a cycloalkyl group of 4 to 5 carbon atoms;

$R^1$ is C—C(=O)—NR$^4$R$^5$, or $L^1$-CN; where $L^1$ is a single bond or $C_1$-$C_8$ alkylene; and $R^4$ and $R^5$ are independently selected from H and $C_1$-$C_8$ alkyl; and $R^2$ is hydrogen or fluoro; where the process comprises the following steps:

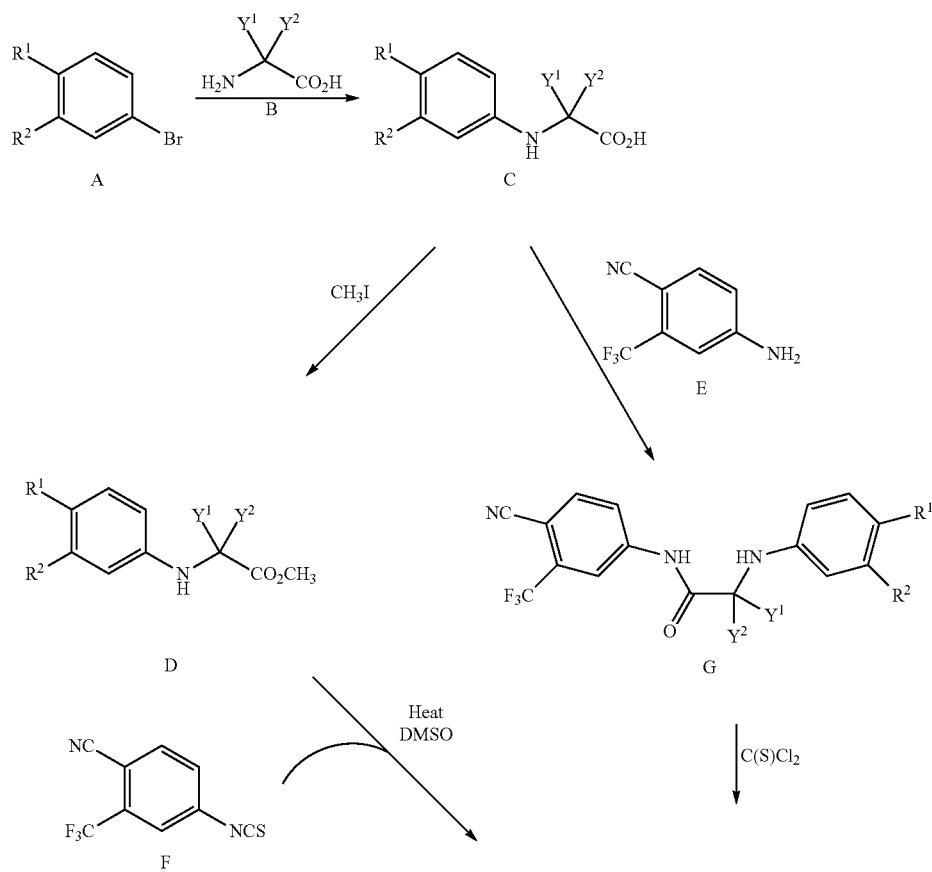

-continued

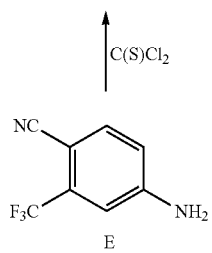

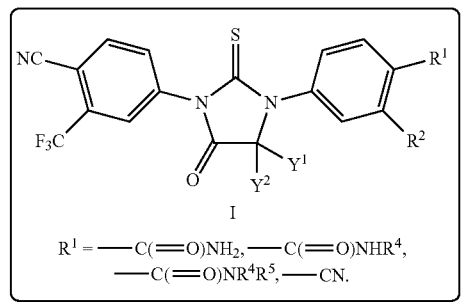

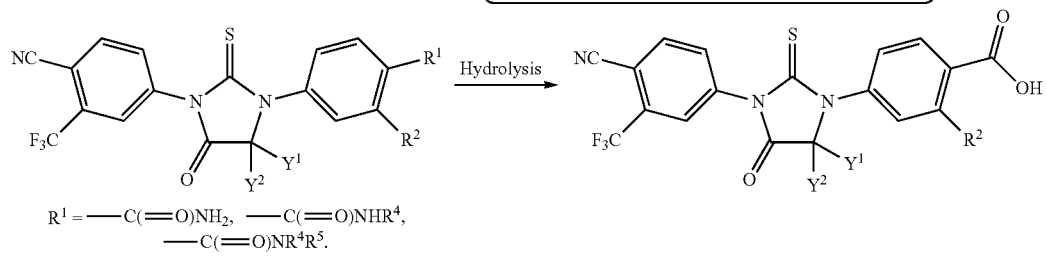

where the synthesis of compound F from compound E is an optional part of the process, and where $CH_3I$ can be replaced by $R^6$-LG, or by $R^6$—OH, where $R^6$ is $C_1$-$C_8$ alkyl and LG is Br, I, or another good leaving group. In one embodiment, $Y^1$ and $Y^2$ are each $CH_3$, $R^1$ is —C(=O)NHCH$_3$ and/or $R^2$ is F. In one embodiment, $Y^1$ and $Y^2$ are each $CH_3$, $R^1$ is —C(=O)NHCH$_3$ and $R^2$ is F. In another embodiment, $Y^1$ and $Y^2$ are each $CH_3$, $R^1$ is —C(=O)NH$_2$, and/or $R^2$ is F. In another embodiment, $Y^1$ and $Y^2$ are each $CH_3$, $R^1$ is —C(=O)NH$_2$, and $R^2$ is F. In another embodiment, $Y^1$ and $Y^2$ are each $CH_3$, $R^1$ is replaced by —C(=O)OH, and/or $R^2$ is F. In another embodiment, $Y^1$ and $Y^2$ are each $CH_3$, $R^1$ is replaced by —C(=O)OH, and $R^2$ is F. In another embodiment, $Y^1$ and $Y^2$, together with the carbon to which they are bonded, form a cyclobutane ring, $R^1$ is replaced by —C(=O)OH, and/or $R^2$ is F. In another embodiment, $Y^1$ and $Y^2$, together with the carbon to which they are bonded, form a cyclobutane ring, $R^1$ is replaced by —C(=O)OH, and $R^2$ is F. In another embodiment, $Y^1$ and $Y^2$, together with the carbon to which they are bonded, form a cyclobutane ring, $R^1$ is —C(=O)NH$_2$, and/or $R^2$ is F. In another embodiment, $Y^1$ and $Y^2$, together with the carbon to which they are bonded, form a cyclobutane ring, $R^1$ is —C(=O)NH$_2$, and $R^2$ is F. In another embodiment, $Y^1$ and $Y^2$, together with the carbon to which they are bonded, form a cyclobutane ring, $R^1$ is —C(=O)NHCH$_3$, and/or $R^2$ is F. In another embodiment, $Y^1$ and $Y^2$, together with the carbon to which they are bonded, form a cyclobutane ring, $R^1$ is —C(=O)NHCH$_3$, and $R^2$ is F.

The synthesis as outlined above comprises a method of synthesizing compound C, which comprises mixing a commercially available variant of compound A with compound B in the presence of a catalytic amount of both a copper (I) catalyst and a ligand such as acetylcyclohexanone, in a polar solvent and with heating of the reaction mixture, followed by cooling, adding water and washing with organic solvent, then acidifying the aqueous layer to isolate the desired product C by precipitation, filtration and drying. Copper catalysts for use in the invention can be chosen from the group consisting of copper (I) chloride and copper (I) iodide. Copper (I) chloride is typically used (Cai et al., Synthesis (Thieme Publishing Group) 2005, No. 3, pp. 496-499).

Compound D can be synthesized by a method which comprises mixing the acid C with an alkylating agent such as methyl iodide and an inorganic base in a polar solvent and a catalytic amount of water, and heating, then cooling the mixture and combining with water, whereupon the product D precipitates from solution and is isolated by filtration and drying. An alternative method for this procedure utilizes standard Fischer esterification conditions comprising mixing acid C in methanol and heating with catalytic mineral acid, followed by isolation as described above. The inorganic base for the alkylation can be selected from the group consisting of potassium carbonate, sodium carbonate, sodium bicarbonate and cesium carbonate, typically potassium carbonate. The mineral acid for the Fischer esterification can be chosen from the group consisting of sulfuric acid, hydrochloric acid, nitric acid and phosphoric acid, typically sulfuric acid.

Initial work on the reaction indicated that the amount of inorganic cations, i.e., residual metal ions, and moisture present in compound D influenced the reaction of compound D with compound F to form compound I. Further development showed that it was actually the presence of residual base which caused undesirable side reactions. However, the inorganic cations serve as useful proxies for the amount of base remaining in preparations of compound D. Procedures to minimize the amount of inorganic cations (such as $K^+$ or $Na^+$) present in compound D—and thus minimizing the amount of base remaining in compound D—were implemented. These strategies included slow and gradual precipitation of product D from its reaction mixture by adding water slowly to the warm reaction mixture, and additional re-suspension or re-slurrying of compound D in water to extract cations. (By "re-slurried" or "re-slurrying" a compound is meant re-forming a slurry of a compound.) Moisture also adversely affects the reaction of compound D with compound F to form compound I. Moisture can be removed from compound D by blowing dry air, dry nitrogen, dry argon, or other dry gas over the compound, by placing the compound on a filter (such as a sintered glass funnel) and pulling air or other dry gas through the compound, or by placing the compound under vacuum for a period of time.

Compound I can be synthesized by mixing compound D with compound F in a mixture of a first polar solvent and a second polar solvent, and heating, then cooling the mixture and combining with water, extracting the desired product with a mixture of a third polar solvent and a fourth polar solvent. The combined organic extract layer is reduced in volume and seeded with crystals of the desired product I to commence crystallization upon cooling, whereupon the crystalline product is isolated by filtration and drying.

The first, second, third and fourth polar solvents can be selected from the group consisting of dimethylsulfoxide (DMSO), dimethylformamide (DMF), N-methylpyrrolidone (NMP), dimethylacetamide (DMA), isopropylacetate (IPAc), isopropyl alcohol (IPA), and the like. In one embodiment of the invention, the first polar solvent is IPAc, the second polar solvent is DMSO, the third polar solvent is IPAc, and the fourth polar solvent is IPA.

The product I can be subjected to the process of crystallization by preparing a saturated solution in an organic solvent or solvent mixture thereof, by concentrating the solution, optionally adding a seed of product I, and cooling the solution to a temperature range and maintaining the solution at that temperature range for a sufficient period till the crystallization of product I is completed. This process of crystallization can be carried out at a temperature range of about 0-80° C., typically 0-10° C.

Compound I can also be synthesized by first treating compound C with a coupling reagent such as dicyclohexylcarbodiimide (DCC), diisopropylcarbodiimide (DIC), 1-ethyl-3-(3-dimethylaminopropyl)carbodiimide (EDCI), and the like, with compound E, in a polar solvent or a mixture of a first polar solvent and a second polar solvent to give compound G, which is then treated with excess thiophosgene with heating to produce compound I. Thiophosgene can be present in an amount of about 1-10 equivalents with respect to compound G, or about 5 equivalents with respect to compound G.

The polar solvent, or first and second polar solvents, can be selected from the group consisting of DCM, DMSO, DMF, NMP, DMA, MeCN, and the like.

Compound I can be subjected to hydrolytic conditions when $R^1$ is a primary, secondary or tertiary amide group, to produce the corresponding carboxylic acid derivative.

In an optional synthetic procedure of the method of the invention, a method for synthesizing compound F is provided which comprises mixing a commercially available variant of compound E with thiophosgene in a mixture of an organic solvent, such as a non-polar solvent, and water at ambient temperature, adding water, and separating the isothiocyanate compound product F. The combined organic extract layer is reduced in volume and a second organic solvent, such as a non-polar solvent, is added to commence crystallization upon seeding with crystals of desired product F, whereupon the crystalline product is isolated by filtration and drying. The organic solvent can be selected from the group consisting of dichloromethane (DCM), toluene, chloroform, hexanes, heptane and 1,4-dioxane, more preferably DCM or heptane. Thiophosgene can be used in the amount of about 1-1.5 mol, such as 1.1 mol, per mole of aniline E. The thiophosgene can be added over a period of time ranging from 30 min to 2 h, such as 1 h.

The product F can be subjected to the process of crystallization by preparing a saturated solution in an organic solvent or solvent mixture thereof, by concentrating the solution, and cooling the solution to a temperature range and maintaining the solution at that temperature range for a sufficient period till the crystallization of product F is completed. The process of crystallization can be carried out at a temperature range of about 0° C. to about 50° C., about 10° C. to about 40° C., about 20° C. to about 30° C., or about 20° C. to about 25° C., or about 25° C. to about 30° C., or about 20° C., or about 21° C., or about 22° C., or about 23° C., or about 24° C., about 25° C., about 26° C., about 27° C., about 28° C., about 29° C., or about 30° C. The organic solvent used for crystallization can be n-heptane, or a mixture of n-heptane and IPAc. For example, about 0.11 mol % to about 0.65 mol % of IPAc in n-heptane can be used, or about 0.20 mol % to about 0.55 mol % of IPAc in n-heptane can be used, or about 0.03 to about 0.06 weight percent of IPAc in n-heptane can be used, or about 0.20, about 0.36, about 0.37, about 0.38, about 0.41, about 0.54, or about 0.55 mol % of IPAc in n-heptane can be used. The crystallization solution of F can be seeded with small amounts of previously isolated F to help induce crystallization, for example about 0.2 to 0.5% by weight of the theoretical amount of F to be obtained. The amount of F used for seeding can range from about 0.20% to about 0.50% (% by weight) of the amount of F sought to be recrystallized, such as about 0.20%, about 0.25%, about 0.30%, about 0.35%, about 0.40%, about 0.45%, or about 0.50%. (For about 20 g of F to be recrystallized, about 0.20% to about 0.50% by weight corresponds to about 40 mg to 100 mg of seed crystal.) After seeding, the solutions/slurries can be cooled to about 0° C. to about 5° C. over a period of about 0.5 to about 2 hours, or about 1 hour. The solutions can also be stirred with high or low agitation, such as from about 200 rpm to about 400 rpm, about 300 rpm to about 400 rpm, about 200 rpm to about 400 rpm, or at about 200, about 300, or about 400 rpm. After crystallization, the solid can then be filtered, washed with cold n-heptane (about 10 to 30 mL, or about 20 mL), and vacuum dried at about 20° C. to about 25° C.

The invention is illustrated by the following non-limiting examples.

EXAMPLES

Experimental

In one aspect of this invention illustrated in Scheme 1, there is provided a new and improved process for the production of 4-(3-(4-cyano-3-(trifluoromethyl)phenyl)-5,5-dimethyl-4-oxo-2-thioxoimidazolidin-1-yl)-2-fluoro-N-methylbenzamide, as described below in Examples 1-5. Materials were obtained from commercial suppliers and were used without further purification. Air or moisture sensitive reactions were conducted under argon atmosphere using oven-dried glassware and standard syringe/septa techniques. The reactions were monitored with a silica gel TLC plate under UV light (254 nm) followed by visualization with a p-anisaldehyde or ninhydrin staining solution; for large scale experiments, reactions were monitored by reverse phase HPLC. Column chromatography was performed on silica gel 60. $^1$H NMR spectra were measured at 400 MHz in CDCl$_3$ unless stated otherwise and data were reported as follows in ppm (δ) from the internal standard (TMS, 0.0 ppm): chemical shift (multiplicity, integration, coupling constant in Hz.).

Example 1

Conversion of 4-bromo-2-fluorobenzoic acid to 4-bromo-2-fluoro-N-methylbenzamide

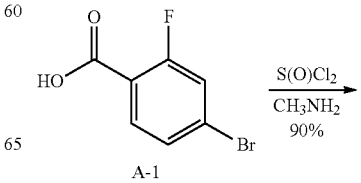

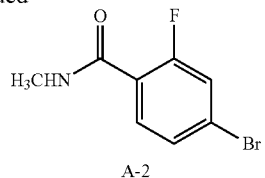

A-2

To a nitrogen flushed 50 L reactor was charged the dry benzoic acid A-1 (1.8 kg, 8.22 mol) followed by isopropylacetate (IPAc) (12.6 L, 7 vol) and DMF (36 mL, 0.02 equiv). To the stirred slurry was added thionyl chloride (689 mL, 9.47 mol, 1.15 equiv) over 5 min (batch warmed from 21° C. to 23° C.). The batch was heated to 60° C. over 2.5 h, maintained at 60-68° C. for 1 h and was sampled for HPLC analysis. The batch was a thin slurry at this point. The conversion to the acid chloride was found to be 99.9% (the acid chloride intermediate was quenched with N-propylamine prior to analysis). After stirring for an additional 1 h at 70-72° C., the batch was cooled to 10° C. over 1 h.

To a nitrogen flushed 30 L reactor was charged aqueous MeNH$_2$ (3.6 L, 41.1 mol, 5 equiv) which was then cooled to 2-10° C. IPAc (3.6 L, 2 vol) was added to the MeNH$_2$ and the MeNH$_2$/IPAc mixture was cooled to 2-10° C. The acid chloride was transferred to the MeNH$_2$/IPAc mixture over 50 min, during which the reaction warmed to 35° C. The reactor that contained the acid chloride was rinsed with IPAc (1.8 L, 1 vol) into the 30-L reactor. The batch was allowed to stir for 15 min at 30-35° C. before sampling for HPLC analysis. The conversion to the product was found to be 100%.

Agitation was ceased and the phases were allowed to separate for 10 min. The green lower layer was removed. The IPAc phase was further washed with water (3 vol followed by 1 vol). The last phase separation was allowed to separate over 14 h at 30° C. After the final separation, the IPAc phase was filtered through a Celite pad which was rinsed with IPAc (3.6 L, 2 vol) to remove the dark green material. The filtrate was then reduced in volume by distillation to 9.5 L (5.3 vol) over 5 h (30-35° C., 100-200 mbar, 1.5-2.9 psi). Precipitation initiated at 8-9 volumes. n-Heptane (18 L, 10 vol) was added to the reactor and the mixture was distilled to 8 L (4.4 vol) over 6 h (30-35° C., 100-200 mbar, 1.5-2.9 psi). At this stage the IPAc/n-heptane ratio was 26:1. The resulting slurry was allowed to stir for 12 h at 25° C. before cooling to 5-10° C. over 1 h. The batch was stirred for 1.5 h at 5-10° C. before filtering, rinsing with n-heptane (2×1 vol) and air-drying. The filter cake (1.87 kg) was vacuum dried at 55-60° C. for 141 h to yield 1.72 kg (90% yield) of desired amide product A-2 with an HPLC purity of 99.5%, and 0.2% H$_2$O.

Example 2

Conversion of 4-bromo-2-fluoro-N-methylbenzamide to 2-(3-fluoro-4-(methylcarbamoyl)phenylamino)-2-methylpropanoic acid

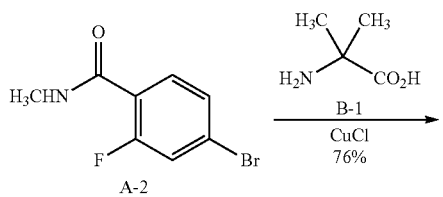

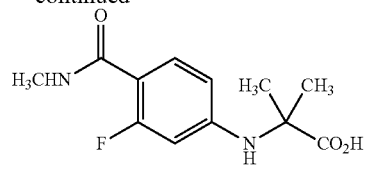

C-1

The bromobenzamide A-2 (10 g, 43.1 mmol), aminoisobutyric acid B-1 (6.7 g, 64.6 mmol, 1.5 equiv), K$_2$CO$_3$ (15 g, 2.5 equiv), 99% CuCl (0.8 g, 8.1 mmol, 0.2 equiv), DMF (60 mL, 6 vol) and water (1.8 mL) were added to the flask and the reaction slurry was heated to 30° C. 2-Acetylcyclohexanone (1.14 mL, 8.1 mmol, 0.2 equiv) was added to the reaction slurry followed by stirring at 105° C. under nitrogen for 12-14 h. HPLC analysis showed 96.6% conversion to the desired product. The reaction mixture was then cooled to RT and extracted with water (120 mL) and IPAc (60 mL). The lower aqueous layer was re-extracted with IPAc (60 mL) and acidified with 180 mL of 1M citric acid to a pH of 4.0. The product began to crystallize at RT and the batch was further cooled to 5-7° C., filtered, washed with water (40 mL) and dried under vacuum at 50° C. for 12 h. The reaction yielded 8.3 g of product C-1 (75.4% yield) as a tan solid with HPLC purity of 99.6%.

Example 3

Conversion of 2-(3-fluoro-4-(methylcarbamoyl)phenylamino)-2-methylpropanoic acid to methyl 2-(3-fluoro-4-(methylcarbamoyl)phenylamino)-2-methylpropanoate

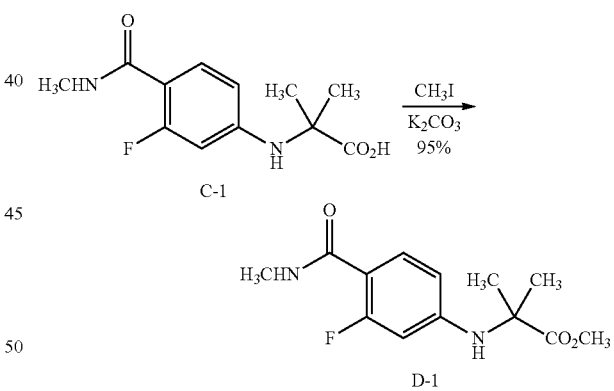

A mixture of methylpropionic acid derivative C-1 (4.0 g, 15.7 mmol), potassium carbonate (2.67 g, 18.8 mmol), DMF (28 mL), and water (0.04 mL) was heated to 30° C. Methyl iodide (1.2 mL, 18.8 mmol) was then added in one portion, and a slight warming of the reaction mixture to 32° C. was observed within 5 min. The mixture was then heated to 40° C. for 1 h. HPLC analysis of the reaction mixture showed >99.9% conversion to ester product. AcOH (0.3 mL) was then added and the resulting mixture was heated to 60° C. followed by addition of water (60 mL) over 50 min maintaining a batch temperature of 58-63° C. The slurry was then cooled to 30° C., the product D-1 was then filtered, and washed with water (2×8 mL). The filter cake was re-slurried in water (40 mL) and rinsed with IPAc (2×8 mL), and dried under vacuum at 45-50°

C. over 16 h yielding 4 g of ester (95% yield) as a pale brown solid with a purity of 99.9%, <0.1% of water and 80 ppm of potassium.

Example 4

Conversion of 4-amino-2-(trifluoromethyl)benzonitrile to 4-isothiocyanato-2-(trifluoromethyl)benzonitrile

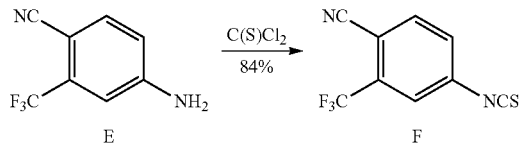

To a nitrogen flushed, 30-L kettle was charged aniline E (4.0 kg, 21.49 mol) followed by n-heptane (9 L, 2.25 vol) and H₂O (10 L, 2.5 vol). The mixture was then agitated for 8 min, cooled to 5-10° C. and thiophosgene (1.81 L, 2.72 kg, 23.64 mol, 1.1 equiv) was charged over 12 min, maintaining the batch temperature at 10-16° C., followed by an n-heptane (1 L, 0.25 vol) rinse. The resulting orange slurry was then warmed to 30-40° C. over 1.5 h and a slight exotherm to a maximum temperature of 46.4° C. was observed. After stirring for 15 h, the orange solution was sampled (>99% conversion). The batch was then heated to 36° C. and the phases were allowed to separate. A rag layer was observed and most of it was purged with the bottom aqueous layer. In two portions, n-heptane (18 L, 4.5 vol) was next charged to the orange heptane layer and the solution was distilled to 1.5 vol (45-46° C., 160 mbar). The solution was diluted once more with n-heptane (8 L, 2 vol) and the batch was distilled to 1.5 vol (45-46° C., 160 mbar). The solution was then diluted with n-heptane (10 L, 2.5 vol), cooled to 30-31° C. (heptane: product F, 5.3:1) and seeded with product F (10 g). Crystallization was visible within 2-3 min after seeding and the slurry was further cooled to 0-10° C. over 3 h and held at 0-10° C. for 2 h. The batch was then filtered, rinsed with filtrate and cold n-heptane (4 L, 1 vol) and dried at 20-25° C., under vacuum, for 13 h to yield product F (4.51 kg, 92%), with an HPLC purity of >99%, and a moisture level of 0.04%.

Example 5

Conversion of methyl 2-(3-fluoro-4-(methylcarbamoyl)phenylamino)-2-methyl propanoate to 4-(3-(4-cyano-3-(trifluoromethyl)phenyl)-5,5-dimethyl-4-oxo-2-thioxoimidazolidin-1-yl)-2-fluoro-N-methylbenzamide

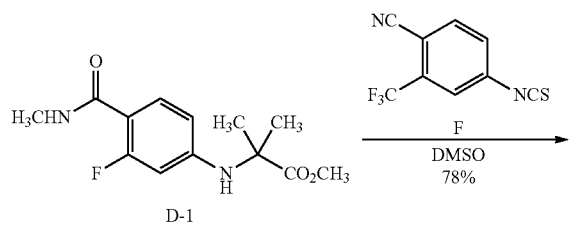

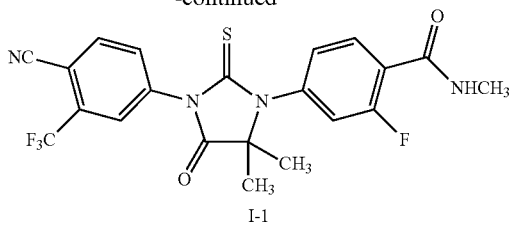

To a round bottom flask was charged methyl ester D-1 (150 g, 0.56 mol), isothiocyanate F (255.6 g, 1.12 mol), DMSO (150 mL, 1 equiv), and IPAc (300 mL, 2 equiv). The mixture was then heated to 83-84° C., stirred for 17.5 h, and then sampled by HPLC to reveal 96.2 A % conversion to the desired product. The reaction mixture was next cooled to 65-70° C. and methanol (22.5 mL, 0.15 vol) was charged. The solution was then stirred for 45 min and cooled to 20-25° C. The solution was next diluted with IPAc (900 mL, 6 vol) and washed with DI water (450 mL, 3 vol) and IPA (225 mL, 1.5 vol) was used to break the emulsion. After extracting the aqueous phase, the organic phase was then concentrated to 4.5 volumes (675 mL) under reduced pressure at 30-35° C. The solution was next diluted with IPA (2000 mL, 13.3 vol) and heated to 75-82° C. (jacket temperature of 95° C.). While heating, the solution was slightly cloudy, but became clear at 70-71° C. The solution was then concentrated to 8 volumes (1200 mL) under atmospheric pressure maintaining 77-82° C. Analysis by ¹H NMR revealed 7.3 mol % IPAc remaining in solution. The solution was then cooled to 77° C., seeded, and cooled over 5 h to 20-25° C. After holding at 20-25° C. for 8 h the batch was then cooled to 0-5° C. over 2 h. After stirring at 0-5° C. for 1 h the slurry was then filtered, washed with IPA (2×225 mL), conditioned with vacuum for 5 min, and then dried under vacuum at 50-55° C. for 117 h. The reaction yielded product I-1 (213.9 g, 82%) as a white powder with 0.14% moisture by KF, >99.9 A % purity by HPLC.

Example 6

Conversion of 4-(3-(4-cyano-3-(trifluoromethyl) phenyl)-5,5-dimethyl-4-oxo-2-thioxoimidazolidin-1-yl)-2-fluoro-N-methylbenzamide to 4-(3-(4-cyano-3-(trifluoromethyl)phenyl)-5,5-dimethyl-4-oxo-2-thioxoimidazolidin-1-yl)-2-fluorobenzoic acid

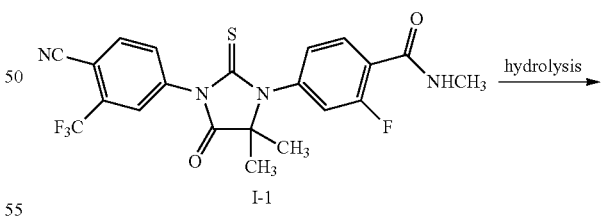

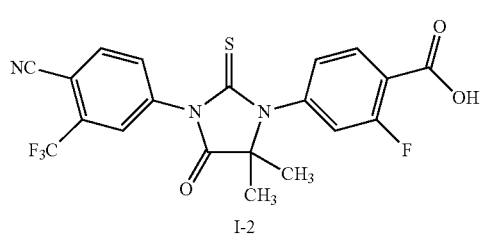

4-(3-(4-Cyano-3-(trifluoromethyl)phenyl)-5,5-dimethyl-4-oxo-2-thioxoimidazolidin-1-yl)-2-fluoro-N-methylbenzamide I-1 was suspended in concentrated HCl and heated at 120° C. in a pressure vessel for 48 h. The reaction was monitored by thin layer chromatography (TLC). The reaction mixture was cooled to ambient temperature. The residue was filtered and purified by silica gel chromatography (100-200 mesh, eluent: 0-5% methanol-dichloromethane) to give the desired carboxylic acid derivative 1-2. MS (m/z): 452 (M+1). HPLC: Column, YMC ODS AQ, 4.6×250 mm, 5 μm, Mobile Phase A: 10 mM Ammonium acetate, Mobile Phase B: Acetonitrile, Gradient, Isocratic: 55% A:45% B, Retention time, 3.804 mM, HPLC Purity, 95.82%, Flow Rate, 1 mL/min. $^1$H NMR (CDCl$_3$, FREEBASE): δ (ppm) 8.22 (t, 1H), 8.0 (d, 1H), 7.98 (s, 1H), 7.82 (d, 1H), 7.2 (m, 2H) 1.6 (s, 6H).

Example 7

Conversion of 2-(3-fluoro-4-(methylcarbamoyl)phenylamino)-2-methylpropanoic acid to 4-(1-(4-cyano-3-(trifluoromethyl)phenylamino)-2-methyl-1-oxopropan-2-ylamino)-2-fluoro-N-methylbenzamide

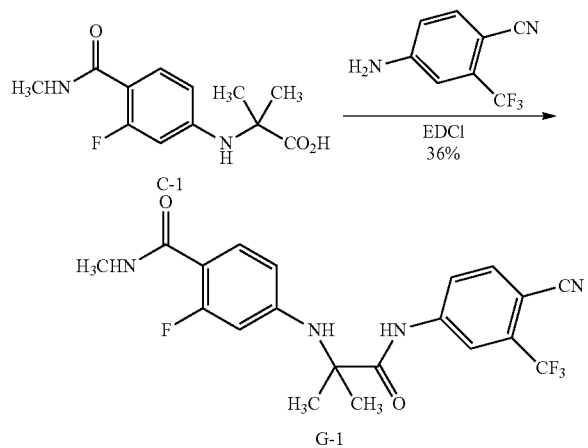

Methylpropionic acid derivative C-1 (0.254 g, 1 mmol) was dissolved in DCM (15 mL) with 1-ethyl-3-(3-dimethylaminopropyl)carbodiimide (0.380 g, 2.0 mmol), followed by slow addition of 4-amino-2-(trifluoromethyl)benzonitrile (0.200 g, 1.1 mmol). The mixture was stirred at RT for 5-6 h. After analysis of the reaction by LCMS and TLC, the mixture was extracted with DCM and the extracts washed with water, dried and evaporated. The crude product was purified by chromatography to yield the desired product G-1 (0.150 g, 36% yield).

Example 8

Conversion of 4-(1-(4-cyano-3-(trifluoromethyl)phenylamino)-2-methyl-1-oxopropan-2-ylamino)-2-fluoro-N-methylbenzamide to 4-(3-(4-cyano-3-(trifluoromethyl)phenyl)-5,5-dimethyl-4-oxo-2-thioxoimidazolidin-1-yl)-2-fluoro-N-methylbenzamide

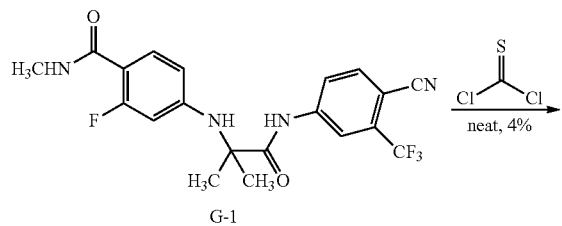

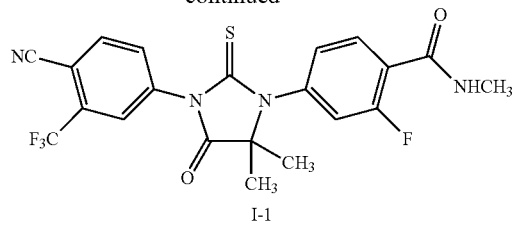

A mixture of amide derivative G-1 (0.1 g, 0.23 mmol) in neat thiophosgene (54 mg, 0.48 mmol) was heated to 100° C. in a sealed-tube for 6 h, then cooled. The mixture was dissolved in DCM, filtered and the filtrate evaporated. The crude material was purified by column chromatography to provide the desired product I-1 (4 mg, 4% yield). Analytical data agree with the compound prepared in Example 5.

Example 9

Syntheses of 4-(1-Carboxy-1-methyl-ethylamino)-2-fluoro-benzoic acid

Example 9A

Synthesis of 4-(1-Carboxy-1-methyl-ethylamino)-2-fluoro-benzoic acid starting from 4-amino-2-fluoro-benzoic acid

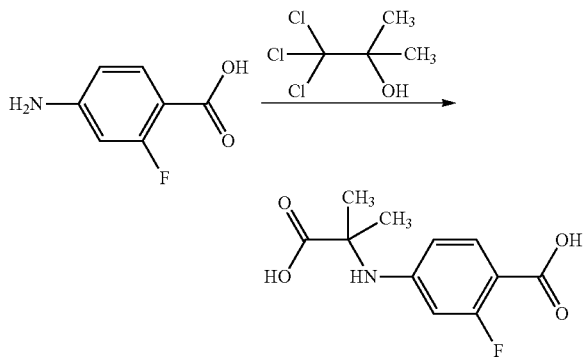

4-Amino-2-fluoro-benzoic acid (0.2 g, 1.29 mmol) and 1,1,1-trichloro-2-methyl-propan-2-ol (0.593 g, 3.35 mmol) were dissolved in anhydrous acetone and the solution was cooled at 0° C. Powdered sodium hydroxide (0.2 g, 5.01 mmol) was added portion-wise after which the reaction mixture was warmed to and stirred at room temperature for 12 h. Volatiles were removed under reduced pressure and the residue was acidified with 1M aqueous HCl. The crude product obtained was purified by reverse phase HPLC to obtain 4-(1-carboxy-1-methyl-ethylamino)-2-fluoro-benzoic acid.

Example 9B

Alternate synthesis of 4-(1-Carboxy-1-methyl-ethylamino)-2-fluoro-benzoic acid starting from 4-bromo-2-fluorobenzoic acid

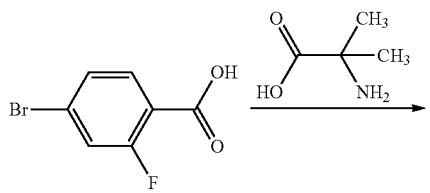

-continued

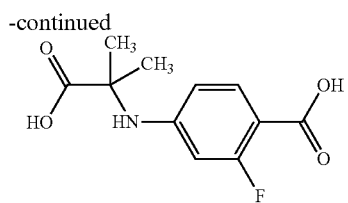

4-Bromo-2-fluorobenzoic acid (20 g, 91.3 mmol), 2-aminoisobutyric acid (14.5 g, 140 mmol), CuI (3.47 g, 18.22 mmol) and K₂CO₃ (31.56 g, 227.91 mmol) were mixed in DMF (200 mL), H₂O (20 mL) and TEA (0.63 mL, 4.54 mmol). To the reaction mixture was then added 2-acetyl cyclohexanone (2.4 g, 17.1 mmol). The reaction mixture was stirred at 90° C. for 14 h. After completion of the reaction water was added. Aqueous layer was washed with ethyl acetate. Aqueous layer was made acidic by adding 1M citric acid solution (pH~4). The product was extracted with ethyl acetate (3×200 mL). Combined organic layer was dried over anhydrous Na₂SO₄, and concentrated under reduced pressure to afford 16 g of 4-(2-carboxypropan-2-ylamino)-2-fluorobenzoic acid as crude product. This crude material was used as such for the next example.

Example 10

Synthesis of 4-[3-(4-Cyano-3-trifluoromethyl-phenyl)-5,5-dimethyl-4-oxo-2-thioxo-imidazolidin-1-yl]-2-fluoro-benzoic acid (Compound M-1)

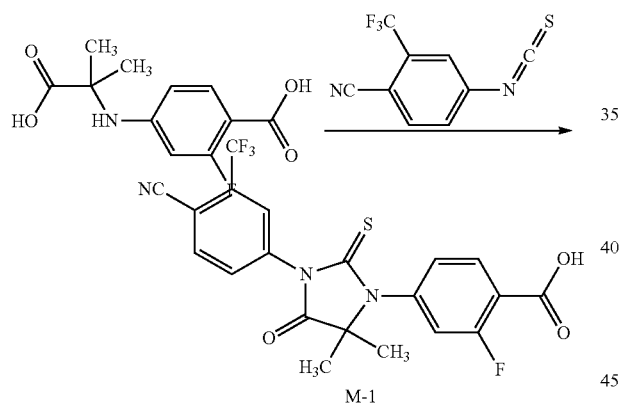

4-(1-Carboxy-1-methyl-ethylamino)-2-fluoro-benzoic acid (241 mg, 1 mmol), 4-isothiocyanato-2-trifluoromethyl-benzonitrile (342 mg, 1.5 mmol) and triethylamine (343 mg, 3.4 mmol) were mixed in EtOH (5 mL) and the solution was stirred for 10 days at room temperature. The reaction mixture was concentrated under reduced pressure, the residue was acidified with 1M aqueous HCl, and the product was extracted with ethyl acetate. The combined organic layer was dried over anhydrous sodium sulfate, and concentrated under reduced pressure. The crude product obtained was purified by column chromatography eluting with ethyl acetate to obtain 4-[3-(4-cyano-3-trifluoromethyl-phenyl)-5,5-dimethyl-4-oxo-2-thioxo-imidazolidin-1-yl]-2-fluoro-benzoic acid (10 mg) as an off white solid.

The disclosures of all publications, patents, patent applications and published patent applications referred to herein by an identifying citation are hereby incorporated herein by reference in their entireties.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

The invention claimed is:

1. A process for preparing a compound of formula (I,2-I):

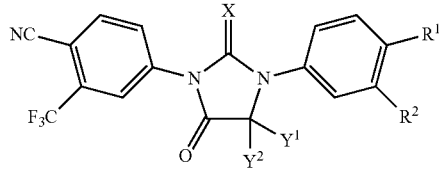

wherein:

X is S or O;

Y¹ and Y² are independently methyl or, together with the carbon to which they are attached, form a cycloalkyl group of 4 to 5 carbon atoms;

R¹ is L¹-C(=O)—NR⁴R⁵, or L¹-CN; where L¹ is a single bond or C₁-C₈ alkylene;

R⁴ is H or C₁-C₈ alkyl;

R⁵ is C₁-C₈ alkyl; and

R² is fluoro;

said process comprising reacting the compound of formula D:

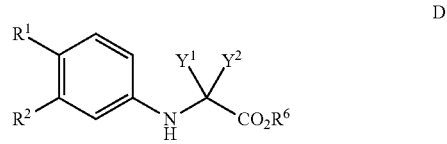

wherein R⁶ is C₁-C₈ alkyl;

with the compound of formula (F,2-F):

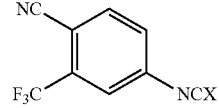

where X is S or O, to yield the diarylthiohydantoin or diarylhydantoin compound of formula (I,2-I):

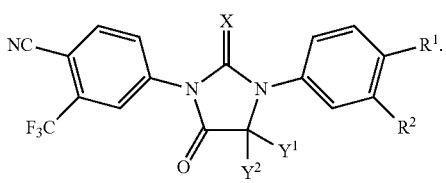

2. A process for preparing a compound of formula (I,2-I):

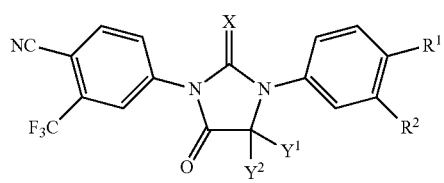

wherein:
X is S or O;
Y¹ and Y² are independently methyl or, together with the carbon to which they are attached, form a cycloalkyl group of 4 to 5 carbon atoms;
R¹ is L¹-C(=O)—NR⁴R⁵, or L¹-CN; where L¹ is a single bond or $C_1$-$C_8$ alkylene;
R⁴ and R⁵ are independently selected from H and $C_1$-$C_8$ alkyl; and
R² is hydrogen or fluoro;
said process comprising reacting the compound of formula A:

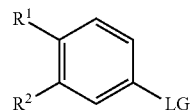

wherein LG is a leaving group, Br, or I;
with the compound of formula B:

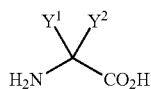

to yield a compound of formula C:

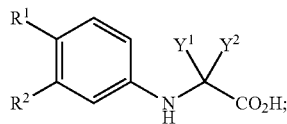

reacting the compound of formula C with a compound of formula R⁶-LG under alkylating conditions or with a compound of formula R⁶—OH under esterification conditions to form the compound of formula D:

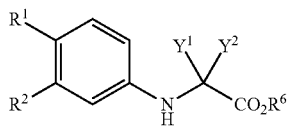

wherein R⁶ is $C_1$-$C_8$ alkyl; and
reacting the compound of formula D with the compound of formula (F,2-F):

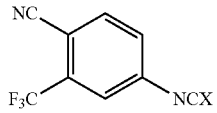

where X is S or O,
to yield the diarylthiohydantoin or diarylhydantoin compound of formula (I,2-I):

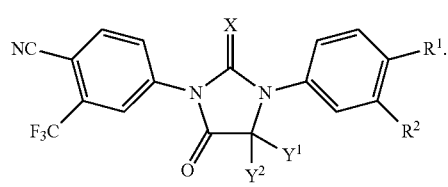

3. The process of claim 1, wherein X is S.

4. The process of claim 1, wherein Y¹ and Y² are both methyl.

5. The process of claim 1, wherein Y¹ and Y² together with the carbon to which they are attached combine to form a cyclobutyl ring or a cyclopentyl ring.

6. The process of claim 1, wherein L¹ is a single bond.

7. The process of claim 1, wherein R¹ is —C(=O)—NHCH₃.

8. The process of claim 1, wherein Y¹ and Y² are both methyl and R¹ is —C(=O)—NHCH₃.

9. A process for preparing a compound of formula (I, 2-Ia):

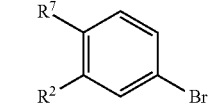

wherein:
X is S or O;
Y¹ and Y² are independently methyl or, together with the carbon to which they are attached, form a cycloalkyl group of 4 to 5 carbon atoms;
R⁷ is C—COOH, where L¹ is a single bond or $C_1$-$C_8$ alkylene and
R² is hydrogen or fluoro; said process comprising reacting the compound of formula Aa:

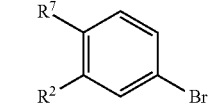

with the compound of formula B:

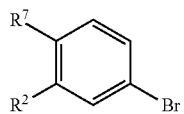

to yield a compound of formula Ca:

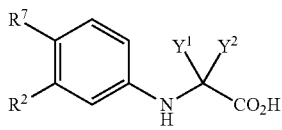

reacting the compound of formula Ca with a compound of formula $R^6$-LG under alkylating conditions or with a compound of formula $R^6$—OH under esterification conditions to form the compound of formula Da:

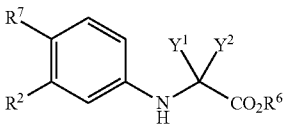

wherein $R^6$ is $C_1$-$C_8$ alkyl;
and reacting the compound of formula Da with the compound of formula (F,2-F):

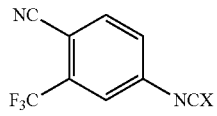

where X is S or O, to yield the diarylthiohydantoin or diarylhydantoin compound of formula (I,2-Ia):

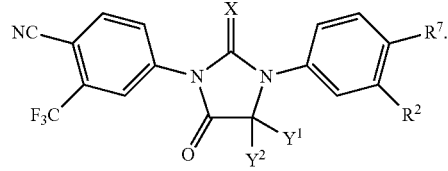

10. The process of claim 9, wherein X is S.

11. The process of 9, wherein $Y^1$ and $Y^2$ are both methyl, $R^7$ is —C(=O)—OH, and $R^2$ is F.

12. The process of claim 2, wherein X is S.

13. The process of claim 2, wherein $Y^1$ and $Y^2$ are both methyl.

14. The process of claim 2, wherein $Y^1$ and $Y^2$ together with the carbon to which they are attached combine to form a cyclobutyl ring or a cyclopentyl ring.

15. The process of claim 2, wherein $L^1$ is a single bond.

16. The process of claim 2, wherein $R^1$ is —C(=O)—NHCH$_3$.

17. The process of claim 2, wherein $R^1$ is —C(=O)—NH$_2$.

18. The process of claim 2, wherein $R^2$ is F.

19. The process of claim 2, wherein $Y^1$ and $Y^2$ are both methyl, $R^1$ is —C(=O)—NHCH$_3$, and $R^2$ is F.

20. The process of claim 2, wherein $Y^1$ and $Y^2$ are both methyl, $R^1$ is —C(=O)—NH$_2$, and $R^2$ is F.

* * * * *